(12) United States Patent
Chung et al.

(10) Patent No.: US 9,957,472 B2
(45) Date of Patent: May 1, 2018

(54) DETERMINISTIC HIGH-DENSITY SINGLE-CELL TRAP ARRAY

(71) Applicant: Georgia Tech Research Corporation, Atlanta, GA (US)

(72) Inventors: Kwanghun Chung, Menlo Park, CA (US); Catherine Rivet, Atlanta, GA (US); Hang Lu, Atlanta, GA (US); Melissa Kemp, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days. days.

(21) Appl. No.: 13/625,836

(22) Filed: Sep. 24, 2012

(65) Prior Publication Data

US 2013/0078163 A1  Mar. 28, 2013

Related U.S. Application Data

(60) Provisional application No. 61/537,895, filed on Sep. 22, 2011.

(51) Int. Cl.
*C12M 3/00* (2006.01)
*C12M 3/06* (2006.01)

(52) U.S. Cl.
CPC .......... *C12M 21/06* (2013.01); *C12M 23/16* (2013.01)

(58) Field of Classification Search
USPC ....................................................... 422/50
See application file for complete search history.

(56) References Cited

U.S. PATENT DOCUMENTS

| | | | | |
|---|---|---|---|---|
| 8,304,230 | B2* | 11/2012 | Toner et al. | 435/288.5 |
| 9,110,026 | B2* | 8/2015 | Collins | G01N 21/6486 |
| 2007/0172903 | A1* | 7/2007 | Toner et al. | 435/7.23 |
| 2011/0117634 | A1* | 5/2011 | Halamish | C12M 23/12 |
| | | | | 435/283.1 |

OTHER PUBLICATIONS

Kobel "Optimization of microfluidic single cell trapping for long-term on-chip culture" The Royal Society of Chemistry 2010, Lab Chip 2010, 10 pp. 857-863.*

(Continued)

*Primary Examiner* — Samuel P Siefke
(74) *Attorney, Agent, or Firm* — Troutman Sanders LLP; Ryan A. Scheider

(57) ABSTRACT

A microfluidic platform for single-cell capture, stimulation, and imaging. It passively traps 4,000 single cells on a 4.5 mm$^2$ footprint in 30 seconds, with a single-cell loading efficiency of 95%. The array format and optimized geometry allows for easy, robust and efficient single-cell loading, while maintaining captured cells in a low shear stress environment for long-term studies. Because cells are captured sequentially, the system is adequate for rare cell samples. Trapped cells can be exposed to various environmental conditions and chemical stimulus and their dynamic response can be monitored over time. The information gained from high-throughput, single-cell time lapsed imaging presents new opportunities in quantifying cellular responses, as averaged information by other measurement methods eliminates sub-population phenotypes.

18 Claims, 58 Drawing Sheets

(56) References Cited

OTHER PUBLICATIONS

Tan "A trap and release integrated microfluidic system for dynamic microarray applications" PNAS 1, 2007 vol. 104, No. 4 pp. 1146-1151.*
Chung "Imaging Single Cell Signaling Dynamics with a Deterministic High-Density Single Cell Trap Array" 2011 American Chemical Society, published Aug. 2, 2011.*
High Density Array of Single Cell Trans of High Throughput Imaging of Calcium Dynamics in Response to Oxidative Stress 14th International Conference on Miniaturized Systems for Chemistry and Life Sciences, Oct. 3-7, 2010.*

* cited by examiner

DETERMINISTIC HIGH-DENSITY SINGLE-CELL TRAP ARRAY

CROSS-REFERENCE TO RELATED APPLICATIONS

This application claims the benefit of U.S. Provisional Application No. 61/537,895 filed 22 Sep. 2011, the entire contents and substance of which are hereby incorporated by reference.

STATEMENT REGARDING FEDERALLY SPONSORED RESEARCH OR DEVELOPMENT

This invention was made with Government support awarded by the National Institutes of Health under agreement numbers NS058465 and CA134299, and the National Science Foundation under agreement number DBI0649833. The Government has certain rights in the invention.

BACKGROUND OF THE INVENTION

1. Field of the Invention

The present invention relates to microfluidic devices for capturing single cells, that can capture cells contained in a sample at one-cell level, methods for separating and capturing cells contained in a sample at one-cell level using a microfluidic device, and methods for quantitatively analyzing gene expression of a single cell utilizing a microfluidic device.

2. Description of the Related Art

Stochasticity in gene expression, protein or metabolite levels contributes to cell-cell variations, the analysis of which could lead to a better understanding of cellular processes and drug responses. Conventional technologies are limited in their throughput, resolution (in space, time, and tracking individual cells instead of population average) and the ability to control cellular environment. A few microfluidic tools have been developed to trap and image cells; however, in most designs presently available, there is a disadvantageous compromise among loading efficiency, speed, the ability to trap single cells, and density or number of trapped cells.

Stochastic effects in gene expression and transcription events in mammalian cells lead to large variations in messenger ribonucleic acid (RNA) copy numbers, causing cell-to-cell variability in genetically identical cells. A current view is that noise arising from stochastic fluctuations plays an essential role in key cellular activities. For example, clonal populations of mouse multipotent progenitor cells or cancer cells have differential fate outcome in response to the same uniform stimulus because of heterogeneities in the dynamics of regulatory proteins, in the expression level of basal signaling proteins, and/or states of proteins regulating apoptosis. Tracking single cell dynamic response is therefore necessary to monitor stochastic fluctuations among cell populations.

At present, such experiments can be technically challenging if the cells of interests are non-adherent, if stimuli need to be delivered, and/or if studies on long time scales are desired. Flow cytometry is often the technique of choice to measure heterogeneity of suspension cell populations, as it can provide high-throughput and can distinguish subpopulations of cells. However, this technology is capable of neither monitoring temporal changes within the same cell, nor distinguishing population from noise due to temporal fluctuation within one cell. Quantitative time lapse microscopy is often required for these measurements, but it presents additional challenges, such as relatively low throughput and movement of the target cells during imaging. It is particularly challenging to image suspension cells. Although one could use adhesion to a solid surface by use of an artificial membrane and receptor binding, this may alter the biological behavior of the cells.

In an attempt to overcome limitations of traditional real-time microscopy, microfluidics has been proposed to allow for increased throughput, control of cell location and extracellular conditions. Various microfluidic techniques have been developed to capture cells, retain them in a specific location, and control the environment surrounding them. Although some of these techniques are quite powerful, even these methods have a limited throughput because the cell traps are spaced sparsely enough such that per view only a small number of cells are captured, and some are difficult to implement, or have side effects or other limitations.

For example, active single-cell capture mechanisms use valves to control flow or dielectric forces with dielectrophoresis (DEP) or optical tweezers to control the location of cells in various environments. Yet the use of dielectric forces on living cells limits cell viability due to buffer cytotoxicity and heat damage.

Passive capturing mechanisms have also been proposed using gravity or fluid flow to direct cells into traps. Most microwell arrays rely on gravity to capture cells. Careful design of the microwells enables up to 70% single cell capture in densely packed wells, but once trapped, exposure to varying chemical solutions and manipulation of the cells are limited because the cells are not actively held in the wells. Flow by diverting streamlines towards traps can also be used to transport and dock cells at specific locations. Once a trap contains cells, fluid towards the trap is significantly reduced, and therefore incoming cells will be diverted to the next empty trap. Optimization of trap dimensions, location and spacing has been performed to increase capture efficiency or single cell trapping. However, in most designs to date, there is a compromise between cell trap density per area and single cell capture efficiency.

What is needed, therefore, is a microfluidic high-density single cell capture, stimulation, and imaging platform that can passively trap thousands of cells relatively quickly with a relatively high single-cell loading efficiency. It is to these needs that the present invention is primarily directed.

SUMMARY OF THE INVENTION

Embodiments of the present invention relate to systems, devices and methods to meet the needs of single-cell imaging studies, comprising a microfluidic platform for high-throughput capture and imaging of thousands of single cells. A preferred trapping mechanism enables over 70% (and more preferably at least approximately 95%) of the traps to be occupied with single cells, with a trap density of 860 traps/mm$^2$. In an exemplary embodiment, the relatively dense array of the present invention allows up to 800 cells to be imaged simultaneously with a 4× objective and a conventional camera setup. Capture occurs with relatively low shear and, for example, up to or over 94% viability after 24 hrs. The present platform is compatible with other upstream microfluidic components for complex cell stimulation patterns, and enables the measurement of, for example, heterogeneity in calcium oscillatory behavior in genetically identical cells, and monitoring kinetic cellular response to chemical stimuli.

The present invention provides high-density and high-efficiency cell traps with a microfluidic high-density single cell capture, stimulation, and imaging platform that accommodates single cells using hydrodynamic flow in conjunction with a careful disposition of the cell traps in an array formed by a serpentine channel. A preferred device passively traps thousands of cells in less than a minute with a single-cell loading efficiency of approximately 95%.

Cells are captured sequentially and deterministically on chip with minimal shear. At low magnification, the trap array enables tracking of hundreds of cells simultaneously over time. At high magnification, spatial information can be resolved on a few precisely located single cells. Imaging can be performed on either live or immunostained cells. Various soluble stimuli can be delivered to the captured cells, and the trap arrays can be relatively easily integrated with upstream microfluidic components capable of multiplexing several experiments on a single chip.

The present invention facilitate quantitative studies of embryogenesis, which require the ability to monitor pattern formation and morphogenesis in large numbers of embryos, time points, and genetic backgrounds. The present invention provides an approach that greatly facilitates these tasks in *Drosophila melanogaster* embryos, one of the most advanced models of developmental genetics. Based on passive hydrodynamics, including inertial effects, the present microfluidic embryo trap array (META) can rapidly order and vertically orient hundreds of embryos. The META platform can be used for the quantitative analysis of multiple morphogen gradients in the dorsoventral patterning system. The present invention is not limited to fixed samples, and can be used for live imaging, and can be adapted for studies of pattern formation and morphogenesis in other model organisms.

The microfluidic platform for single-cell capture, stimulation, and imaging is capable of passively trapping 4,000 single cells on a 4.5 mm2 footprint in 30 seconds, with a single-cell loading efficiency of 95%. The array format and optimized geometry allows for easy, robust and efficient single-cell loading, while maintaining captured cells in a low shear stress environment for long-term studies. Because cells are captured sequentially, the present system is adequate for rare cell samples.

Compared to conventional designs, the higher cell trap density allows for imaging of increased cell numbers, therefore increasing throughput of single cell experiments, while being compatible with high resolution imaging at high magnification. Trapped cells can be exposed to various environmental conditions and chemical stimulus and their dynamic response can be monitored over time.

The information gained from high-throughput, single-cell time lapsed imaging presents new opportunities in quantifying cellular responses, as averaged information by other measurement methods eliminates sub-population phenotypes. The ease of use of the present system means it will be used for diverse applications, such as fundamental studies of stochastic behavior, diagnosis of patient samples, or drug screens in cancer biology and stem cell biology.

In an exemplary embodiment, the present invention is a microfluidic cell trap array comprising a cell-delivery channel having an inlet and an outlet, and cell traps formed in the channel, wherein the cell trap array has a density of greater than 700 traps/cm$^2$. The cell trap array can have a density of greater than 800 traps/mm$^2$.

The cell trap array can have a loading efficiency of greater than 70%. The cell trap array can have a loading efficiency of greater than 90%.

The cell-delivery channel can comprise a generally serpentine channel, and the generally serpentine channel can comprise a plurality of generally parallel subchannels connected to one another via subchannel end portions. The subchannel end portions can an appropriate curvature such that the generally serpentine channel with a plurality of generally parallel subchannels provides for a generally uniform medium flow rate therethrough.

In another exemplary embodiment, the present invention is a microfluidic single-cell trap array comprising a cell-delivery channel having an inlet and an outlet, the cell-delivery channel forming a serpentine channel including a plurality of switchback subchannels connected to one another via subchannel end portions, and a plurality of single-cell traps formed in at least a portion of the total number of subchannels, wherein the single-cell trap array has a density of greater than 700 traps/cm$^2$, and wherein the single-cell trap array has a loading efficiency of greater than 70%.

In at least a portion of the total number of subchannels having single-cell traps, such subchannels can have a cell trapping zone along the length of the subchannel, and a cell focusing zone on at least one side of the cell trapping zone. Subchannels having a cell trapping zone can have a cell focusing zone on both sides of the cell trapping zone.

The cell trapping zone can comprise at least a portion of the single-cell traps, the single-cell traps sized to capture a single cell, and the cell focusing zone comprising flowthrough apertures sized so as not to capture a cell flowing therethrough.

In another exemplary embodiment, the present invention is a microfluidic single-cell trap array comprising a cell-delivery channel having an inlet and an outlet, the cell-delivery channel forming a serpentine channel including a plurality of switchback subchannels connected to one another via subchannel end portions, at least a portion of the total number of subchannels having a cell trapping zone along the length of a subchannel, the cell trapping zone bounded by a leading cell focusing zone and a trailing cell focusing zone, each cell trapping zone comprising a plurality of single-cell traps sized to capture a single cell, and each cell focusing zone comprising a plurality of flowthrough apertures sized so as not to capture a cell flowing therethrough, such that media having cells traveling through a subchannel having a cell trapping zone will experience both a flow parallel to the length of the subchannel to carry cells through the array, and a normal flow moving travelling cells closer to the traps in the cell trapping zone after passing the leading cell focusing zone. The single-cell trap array has a density of greater than 700 traps/cm$^2$, or more preferably, a density of greater than 800 traps/mm$^2$. The single-cell trap array can have a loading efficiency of greater than 70%, or more preferably, a loading efficiency of greater than 90%.

At least a portion of the single-cell traps can have a geometry engineered so that traps experience similar flow rates near one another in order to provide a generally uniform trapping condition for each trap.

At least a portion of the single-cell traps can have a geometry engineered so that once a cell occupies a trap, it physically excludes another cell from being trapped in the same trap.

At least a portion of the single-cell traps can have a geometry engineered so that once a cell occupies a trap, neither the media flow through the single-cell trap array nor another cell can dislodge a trapped cell.

In the microfluidic single-cell trap array, wherein after passing a cell focusing zone, travelling cells in proximity to a single-cell trap can experience two flows, a main stream (Q) flowing in the direction of the cell-delivery channel, and a directing stream (q) directing the cell into a single-cell trap, and wherein the ratio Q/q is engineered to guide cells into non-occupied traps, and once all traps in a subchannel having a cell trapping zone contain trapped cells, travelling cells pass a downstream cell focusing zone, and travel to a next subchannel.

In another exemplary embodiment, the present invention is an array chip for high resolution imaging of cellular features and activities. The present microfluidic platform can successfully capture and immobilize both fixed and live cells. Trapping and perfusion rates do not induce undesirable shear stress for long-term studies. Viability was observed to be uniform throughout the present trap array chamber, suggesting the absence of high shear stress zones in the chamber and the compatibility of the chip with long-term dynamic studies. The high trap density allows for imaging large number of cells. The present microfluidic chip is also compatible with immunostaining.

In another exemplary embodiment, the present invention is a microfluidic array for large-scale ordering and orientation of embryos, which enables high-throughput analysis of the DV patterning signals with an array in which hundreds of embryos are oriented vertically in a matter of a few minutes. Such "end-on" orientation allows for the entire DV axis data to be collected from multiple embryos easily. With an easy-to-use META device according to the present invention, a fluid carrying hundreds of embryos is injected into the device using a simple pressure source. In a few minutes, the fluid flow directs the embryos into the traps, and the device with the loaded embryos can be mounted onto a microscope stage or stored for future use.

The present invention can be used to quantify morphogen gradients in fixed embryos and to monitor nuclear divisions in live embryos. The design enables high-throughput analysis of the dorsoventral patterning system at the level of the inductive cues and their signaling and transcriptional targets in the wild type and mutant backgrounds.

These and other objects, features and advantages of the present invention will become more apparent upon reading the following specification in conjunction with the accompanying drawing Figures.

BRIEF DESCRIPTION OF THE FIGURES

The various embodiments of the invention can be better understood with reference to the following drawings. The components in the drawings are not necessarily to scale, emphasis instead being placed upon clearly illustrating the principles of the various embodiments of the present invention. In the drawings, like reference numerals designate corresponding parts throughout the several views.

FIG. 1 is an optical micrograph of a trap array fabricated using soft lithography;

FIG. 2 illustrates a magnified view of the details of cell trap design (boxed region in FIG. 1). The inset (upper right corner) shows dimensions of a single trap. Scale bar, 10 µm;

FIG. 3 is an overlay of phase contrast and fluorescent images showing single cells trapped in an array;

FIG. 4 is a schematic drawing of three columns of the array showing trajectory of cells. Cell suspension enters the array from the top-left and exit to bottom-right. Dotted lines represent trajectory of cells;

FIG. 5 illustrates a magnified view of the details of the boxed region in FIG. 4, showing a cell focusing mechanism. Converging flow (upper row of arrows) and diverging flow (lower row of arrows) through dummy traps focus cells toward the traps;

FIG. 6 illustrates a magnified view of the details of the boxed region in FIG. 5, illustrating two major streams that cells experience, a main stream (Q) flowing along the delivery channel, and a directing stream (q) directing the cell into the trap;

FIG. 7 is an overlay of a series of 1045 images showing cell trajectories during loading.

FIG. 8 is a schematic representing the variables involved in loading efficiency optimization;

FIG. 9 is plot showing probability of trap occupancy (circles) and probability of single-cell occupancy (diamonds) in varying ratios of resistances ($R_{ch}/R_{trap}$). FIGS. 10-12 are representative micrographs of cell trapping:

FIG. 10—$R_{ch}/R_{trap} \sim 110$;

FIG. 11—$R_{ch}/R_{trap} \sim 255$;

FIG. 12—$R_{ch}/R_{trap} \sim 500$.

FIG. 13 is a fluorescent microphotograph of two cell trap chambers (boxed areas);

FIG. 14 is a fluorescent image of immunostained Jurkat cells with confocal microscopy (100×). In color drawings, blue is for Hoechst for the nucleus, in green, calnexin, an ER-bound protein, and in red, profilin-1, a cytoplasmic protein;

FIG. 15 shows calcium dynamics in resting Jurkat cells: 216 cells are imaged every three seconds for 15 minutes. Each line corresponds to an individual cell in the array. The heat map indicates, in color drawings, low (in blue) to high (in red) intracellular calcium concentration.

FIG. 16 is a microphotograph of cell trap arrays interfaced with a concentration gradient generator. The numbers represent the chamber number;

FIG. 17 shows an average single cell calcium response for different concentrations of ionomycin. The inset shows the linearity of the concentration gradient (n=4);

FIG. 18 shows a single cell response to ionomycin. Each line of the heat map corresponds to the dynamics of a single cell. The heat map is subdivided into eight smaller heat maps, which correspond to decreasing ionomycin concentrations (cf, TABLE 1 for details about number of cells imaged and ionomycin concentration). In each subset, unsupervised clustering has been performed to cluster cells with similar responses;

FIG. 19 provides traces of single cell responses to 2.5 µM ionomycin. In color drawings, the red line corresponds to the average response ±SEM. The black arrow represents time of ionomycin addition.

FIG. 29(a) provides a geometry of the channels and finite element mesh used in numerical simulations. To simplify the numerical simulations, only six columns of the serpentine channel are used, and the trap is assumed as a rectangular rod;

FIG. 30 shows volumetric flow rate in the serpentine main channel at each trap;

FIG. 32 shows volumetric flow rate through the cross-flow channels at each trap;

FIGS. 33-34 show dean flow and the converging and diverging flow along the cross-flow channels focus the embryos towards the traps, wherein FIG. 33 is a numerical model showing flow stream line in the turn, and FIG. 34 includes optical images showing an embryo migrates along the wall of the serpentine channel where the traps are located. The scale bar is 800 μm.

FIG. 31(a) is a numerical simulation showing hydrodynamic force on the surface of an embryo simplified as a rectangular rod, and FIG. 31(b) illustrates the torque generated by hydrodynamic force when an embryo is located inside of a trap with various angles.

FIG. 35 includes the reconstructions at 0 psi, and FIG. 36, at 6 psi (loading pressure). The middle images in FIGS. 35-36 are single frames from the middle of the device. Dotted circles represents the DV plane of an embryo. The bottom images of FIGS. 35-36 are confocal images showing cross-sectional profiles of the trap opening. Dotted ellipses represent a vertically oriented embryo. The scale bars are 100 μm.

FIGS. 37(a)-(c) characterize trapping efficiency, wherein FIG. 37(a) is an optical image showing trapped embryos through the entire device, FIG. 37(b) is a graph of rapping efficiency in each column, and FIG. 37(c) is a graph of the trapping efficiency in each row. The error bars represent standard deviation. n=4 independent trials.

FIG. 49 illustrates average gradients for both genetic backgrounds shown with the standard error of mean.

FIG. 50 is a simplified view of the DV patterning network, showing the feedforward loops activated by Dl. Briefly, Dl activates the expression of Twist, which acts together with Dl to activate the expression of transcription factor Snail (Sna). Dl also acts as a transcriptional repressor of dpp, a ligand in the Drosophila BMP signaling pathway, which patterns the dorsal ectoderm. The joint action of the Dl, Twi, and Sna proteins specifies the lateral expression patterns of rhomboid (rho) and vein (vn), components of the EGFR signaling pathway, which signals through the ERK/MAPK pathway in the presumptive neuroectoderm.

FIGS. 51-53 are confocal images of embryos stained with antibodies that recognize Dl and Twi (FIG. 51), Dl and phospho-MAPK (dpERK) (FIG. 52), and Dl and phospho-MAD (pMAD) (FIG. 53). The scale bar represents 25 μm.

FIGS. 54-56 show averaged gradients of pMAD (FIG. 54), Twist (FIG. 55), and dpERK (FIG. 56) plotted with standard error. The numbers of embryos used in the analyses are 32, 20, and 19, respectively.

FIG. 57 contains frames of an embryo undergoing nuclear divisions. FIG. 58 contains frames of an embryo undergoing ventral invagination. For both videos, images were taken 70 μm from the anterior pole. The scale bar represents 25 μm.

DETAILED DESCRIPTION OF PREFERRED EMBODIMENTS

Figure 1:
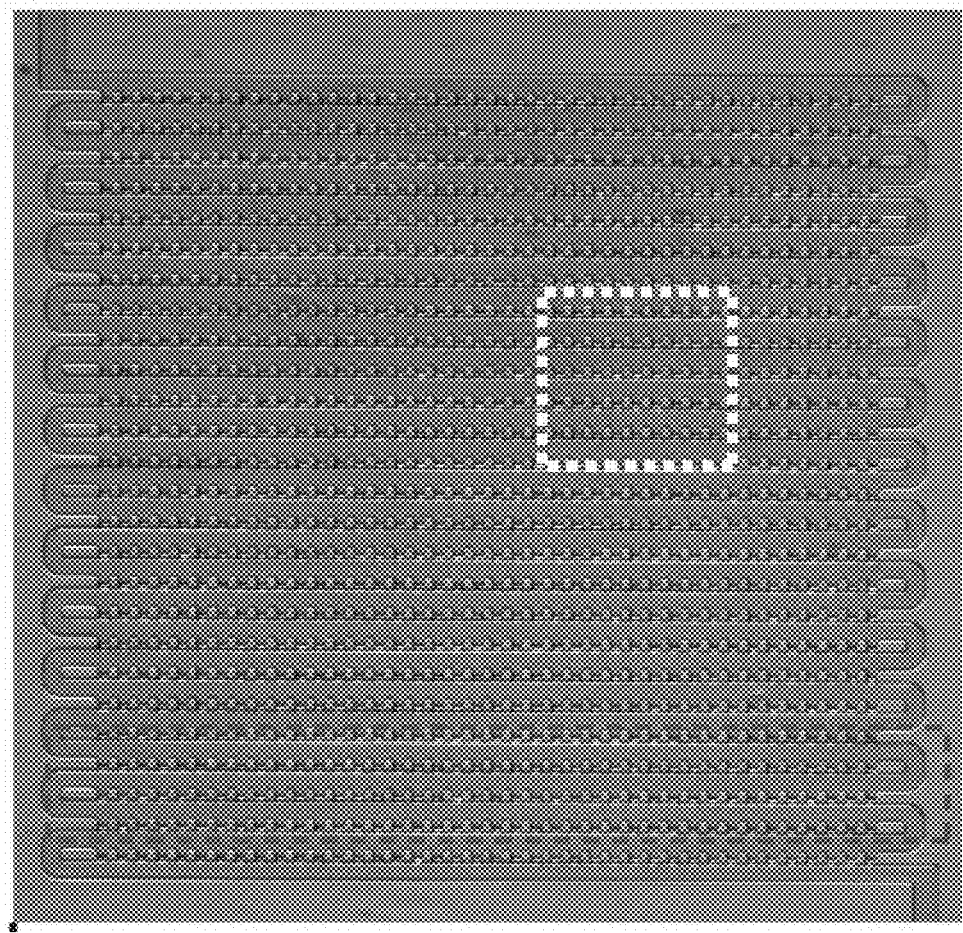
FIGS. 1-7 illustrate the design and principle of single cell trapping array according to exemplary embodiments of the present invention, where.

Although preferred embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, another embodiment includes from the one particular value and/or to the other particular value.

By "comprising" or "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Imaging Single-Cell Signaling Dynamics with a Deterministic High-Density Single-Cell Trap Array Preferred Methods and Materials
Fabrication of Polydimethylsiloxane (PDMS) Devices
The present microfluidic devices were fabricated using soft lithography. Negative molds were fabricated by UV photolithographic processes using a negative photoresist (SU8-2010, 14-16 μm, and SU8-2002, 1.5-3 μm in thickness) (Microchem, Newton, Mass.). Patterned wafers were then treated with tridecafluoro-1,1,2,2-tetrahydrooctyl-1-trichlorosilane vapor (United Chemical Technologies, Bristol, Pa.) in a vacuum desiccator to prevent adhesion of PDMS (Sylgard 184, Dow Corning, Midland, Mich.) before the molding process. PDMS mixture of A and B in a 10:1 ratio was poured onto the mold to obtain a 5 mm thick layer, which was then fully cured at 70° C. for two hours. The PDMS was peeled off the mold and individual devices were cut to size. Medical grade polyethylene (PE3) tubings (Scientific Commodities) were used for fluidic connections. Holes for fluidic connections were punched with 19 gauge needles. PDMS devices were plasma bonded onto either a cover glass or slide glass depending on applications.

Cell Culture, Stimulation and Staining
Jurkat E6-1 human acute T cell lymphoma cells (ATCC) were cultured in RPMI 1640 medium with L-glutamine (Sigma-Aldrich, St. Louis, Mo.) with 10 mM HEPES, 1 mM sodium pyruvate, 1×MEM nonessential amino acids, and 100 units $mL^{-1}$ penicillin streptomycin (Cellgro), supplemented with 10% certified heat inactivated fetal bovine serum (Sigma-Aldrich, St. Louis, Mo.), at 37° C. in a humidified 5% $CO_2$ incubator. For nuclei visualisation, Jurkat cells were incubated with Hoechst 33258, at a final concentration of 1 μg $mL^{-1}$, at 37° C. for 20 minutes.

Cells were checked for viability using Live/Dead stain (Invitrogen) following the manufacturer's protocol. For high resolution microscopy, $10^6$ cells were fixed in a 5% formalin solution (Sigma-Aldrich, St. Louis, Mo.) for 15 minutes at 37° C., washed three times with cold PBS, and resuspended in 100 μL of ice cold 90% methanol. Immunostaining was performed on fixed cells using Hoechst 3342 for DNA staining, mouse α-calnexin (Abcam) for ER staining, and rabbit α-profilin-1 (Cell Signaling), as a cytoplasmic localized protein. Incubation with the primary antibody for one hour at room temperature was followed by three wash steps with a solution of 2% BSA in PBS and incubation for 40 minutes at room temperature with the following secondary antibodies: Alexa 488 α-mouse (Invitrogen) and goat α-rabbit TRITC (Southern Biotech). To monitor calcium signaling, Jurkat cells were incubated with 5 μM Fluo-3 (Invitrogen) for 20 minutes at 37° C., washed with cold PBS, and loaded into the cell traps. Trapped cells were stimulated with ionomycin (Sigma, St. Louis, Mo.) at various concentrations to release intracellular calcium.

Microfluidic System Operation
Before each experiment, the microfluidic devices were primed using a solution of 2% BSA in PBS to remove any air bubbles and limit undesirable cell adhesion to the wall. A pressure difference of 3.5 kPa (5.5 kPa for devices with upstream serial-dilution gradient generator) created by gravity was used to drive the flow, resulting to an average flow rate of ~2 μL $h^{-1}$. Cell loading was obtained by pipetting 2 μL of 5×$10^6$ cell $mL^{-1}$ of cell suspension on the chip positioned on the microscope stage. Further experiments (staining, stimulation) were performed by adding 5 μL of 4× chemicals in the inlet hole and flowing over the trapped cells for the desired time. All experiments were performed in a microcontrolled environment (temperature set at 37° C. in a humidified 5% $CO_2$ environment).

Quantification of the Trapping Efficiency
To determine trapping efficiency, devices with varying geometries were built (FIGS. 8-12). The height of the main channel ($h_{mc}$) was varied from 14 to 16 μm. Width of the traps (w) was varied from 8 to 15 μm. The length of the narrow microchannel (L) was varied from 3.3 to 8 μm. The height of the narrow microchannel ($h_{gap}$) ranged from 1.5 to 3 μm. Conserved lengths are: width of the main channel (30 μm), total width of a trap (pocket and wall included: 25 μm) as well as total length of the trap (20 μm). Resistance of the main channel above a trap was estimated by:

$$R_{ch} = \frac{30}{25 * h_{mc}^3} \quad (1)$$

and resistance of the trap by:

$$R_{trap} = \frac{20 - L}{w * h_{mc}^3} + \frac{L}{w * h_{gap}^3} \quad (2)$$

Data Collection and Analysis

High resolution microscopy was performed on a 2-photon confocal microscope (Zeiss LSM 510 NLO). Time-lapse microscopy and device characterization experiments were performed on an epifluorescent (Nikon Eclipse Ti) microscope with an environment controlled chamber. Images from individual chambers were captured sequentially using an automated XYZ stage with a 0.7 second delay between each chamber.

Custom Matlab® (MathWorks) scripts were written for semi-automated image processing. Briefly, images were cropped to contain the cell trapping area and a mask of the traps drawn from each picture by finding the areas of higher intensities. The ratio of the number of objects in the overlay of the mask on the original picture to the number of traps corresponds to the percentage of traps occupied. To discriminate traps occupied by a single versus multiple cells, several features were measured for each object, including area, convex area, eccentricity, solidity, perimeter, extent and orientation.

A principal least square analysis (SIMCA-P, Umetrics) was run on a known dataset of objects to determine the two most informative predictors of the number of cells contained in an object. The perimeter and the extent (ratio of pixels in the object to pixels in the total bounding box) were found as being the most informative. To quantify single cell trapping efficiency, the distribution of objects in the perimeter-extent space was fitted to a 2-component Gaussian mixture model for each chamber trap array. The maximum likelihood parameters from each of the two subpopulations were retrieved and represented respectively the percentage of single cell objects and multiple cell objects. Single cell response intensities were obtained by tracking the mean intensity of each object considered as a single cell in the overlaid mask and image over time.

Results and Discussion

Design of an Efficient Microfluidic Single-Cell Trap Array

To allow imaging of a large number of cells in a field of view, single cells need to be arranged with high efficiency and with uniform trapping conditions in an array of densely packed traps. To satisfy these requirements, design principles developed for high-density embryo trapping were adapted, and achieved capture of 4,000 single cells on 4.5 mm² in 30 seconds, and with a loading efficiency over 95%.

Figure 2:
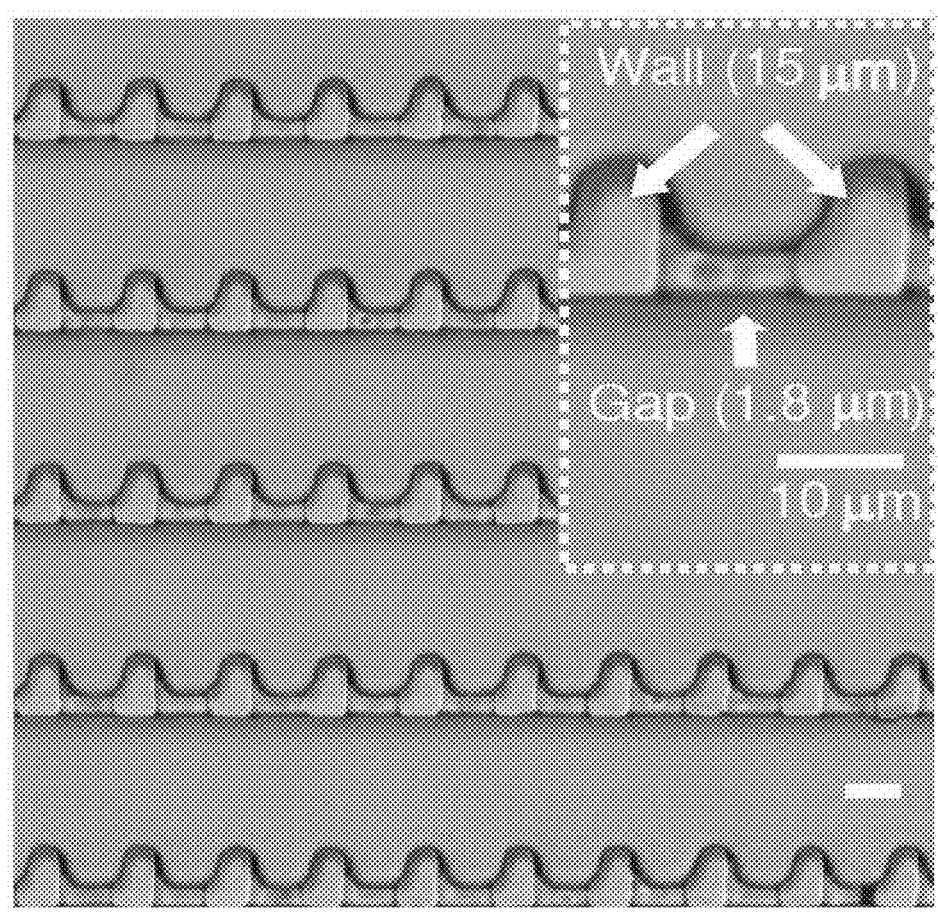
Figure 3:
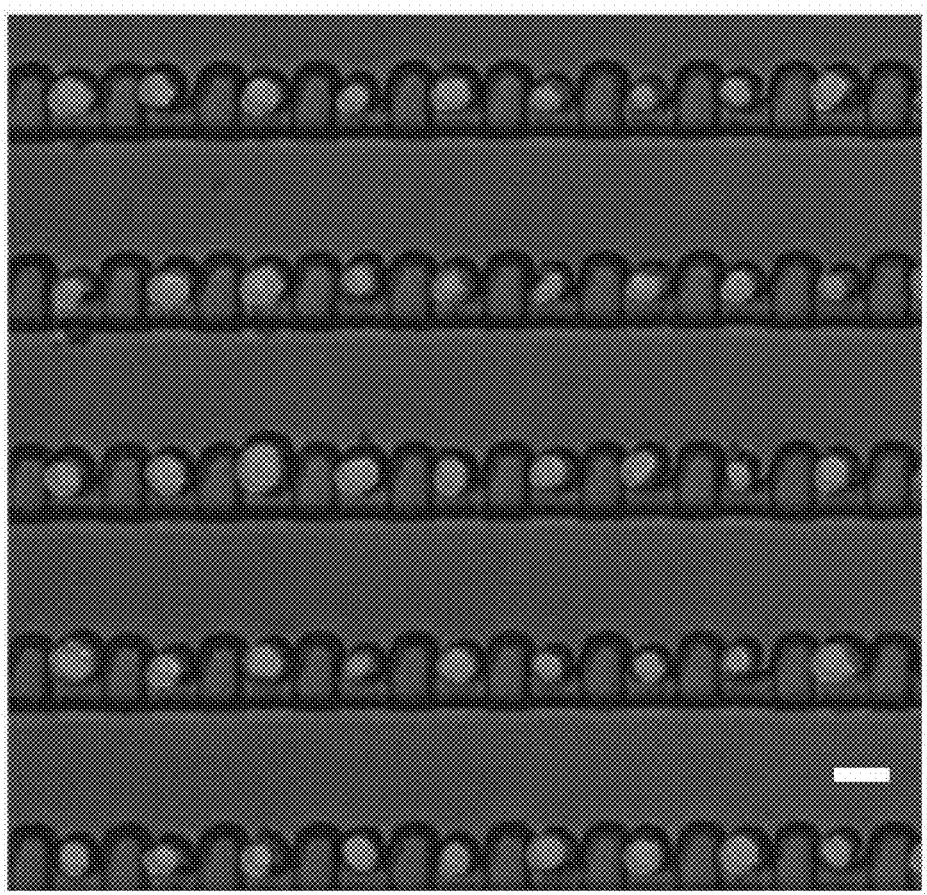
Figure 4:
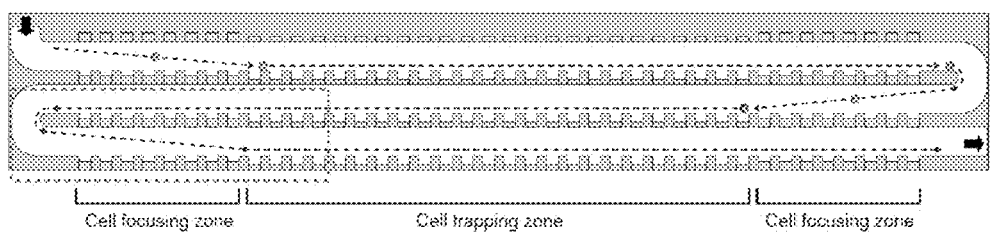

The microfluidic devices made from one layer of polydimethylsiloxane (PDMS) comprise arrays of highly packed single cell traps (FIGS. 1-7). Each array comprises a wide serpentine cell-delivery channel arranged in 26 column format and an array of cross-flow channels that connect each section of the serpentine channel (FIGS. 1-2). The width (~25 µm) and height (14 µm) of the cell-delivery channel are large enough to ensure cells easily moving without clogging. Each column includes 24 single cell traps (FIG. 2-3) in the middle and eight dummy traps at each end (FIG. 4). The size of the cell trap is similar to that of cell of interest so that once a cell occupies a trap, it physically excludes the next cell and reduces the probability of trapping more than one cell. The cell traps are connected to the 1.8 µm deep shallow cross-flow channels (FIG. 2 inset). By minimizing space between neighboring traps (~8 µm in a column, ~33 µm between columns), a density of 860 traps/mm² was achieved, which is 2-3 orders of magnitude higher than what has been previously reported for deterministic single cell traps (175~700 traps/cm²).

Figure 5:
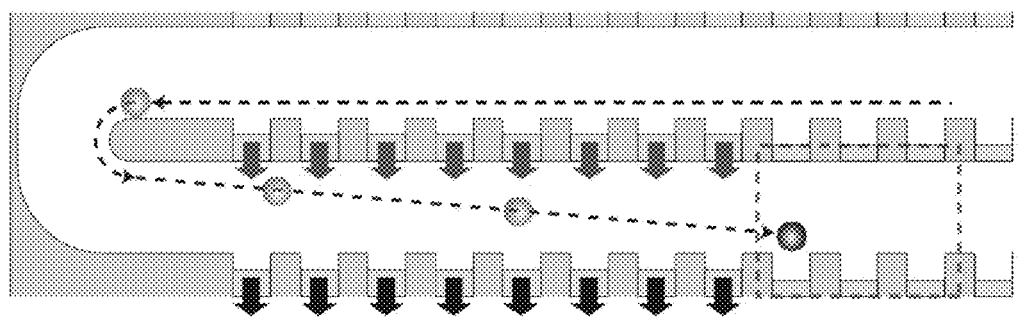
Figure 6:
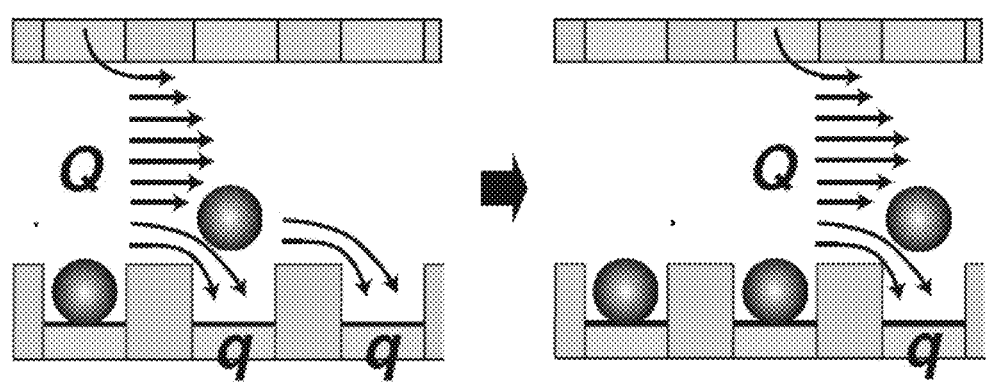
Figure 7:
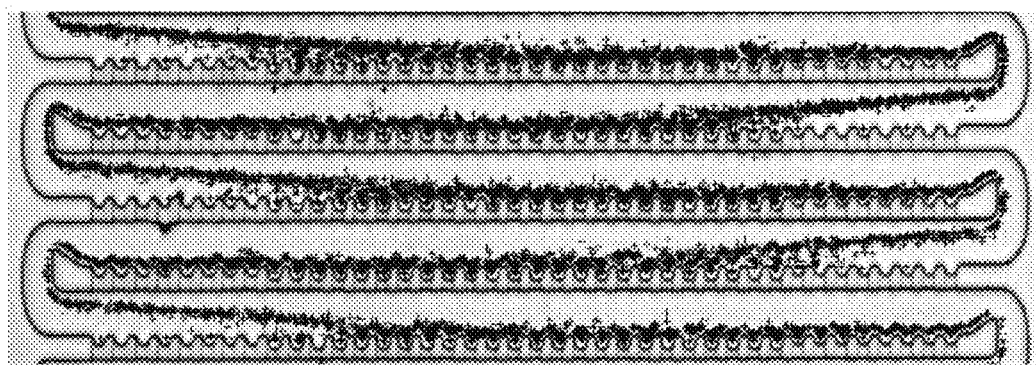
Figure 8:
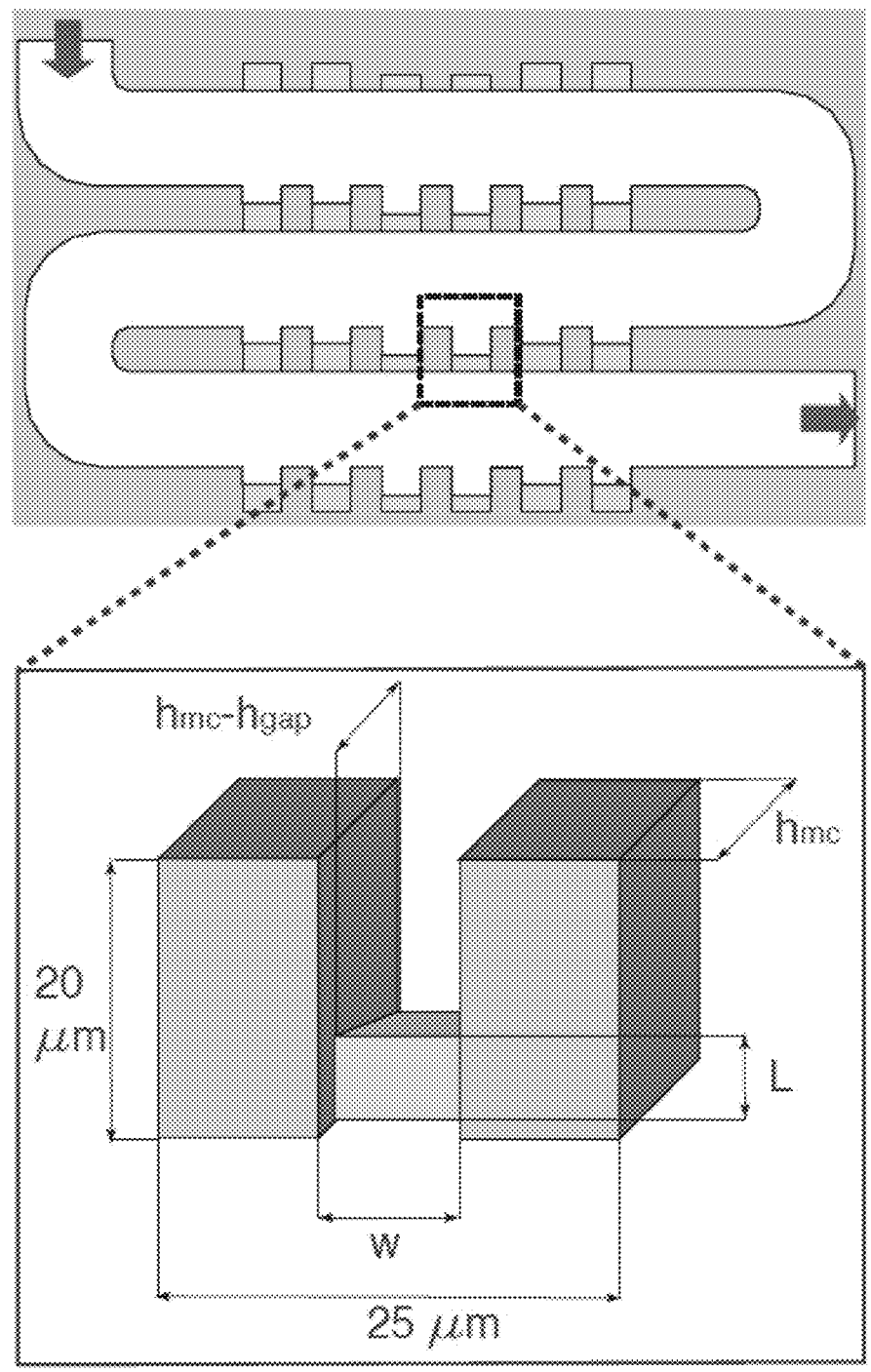
FIGS. 8-12 illustrate trapping efficiency of devices with various geometric dimensions according to exemplary embodiments of the present invention, where.

If flow through the traps has large variations throughout the array, the trap occupancy will be severely compromised. To make the trapping condition uniform, the geometry of the channels were engineered so that cells experience similar flow rates near each trap. Cells passing the focusing zones along the wide delivery channel are focused toward the traps by diverging (lower arrows in FIG. 5) and converging flow (upper arrow in FIG. 5) through the dummy traps (FIGS. 5-6). The number of the dummy traps is optimized to make cells move closer to the trap after passing the focusing zone. This increases the frequency with which cells contact the traps and are loaded into them (FIG. 7).

After passing the focusing zone, cells close to a trap experience two streams; a main stream (Q) flowing along the delivery channel and a directing stream (q) directing the cell into the trap (FIG. 6). If the Q/q is in a proper range, cells can be guided into the trap and docked. Once all the traps in one row are occupied, extra cells pass another cell focusing zone without getting trapped and move to the next row. Despite the proximity of the dummy traps, cells are not captured because the size of the dummy traps is smaller than that of the cells. By optimizing various geometric parameters, such as the width and height of the channels and the number of traps, over 95% single cell trapping efficiency was achieved throughout the device (FIG. 3).

Optimization of Single Cell Loading Efficiency

Geometries of the docking sites were optimized in order to deterministically trap a single cell per trap. A cell close to a trap experiences forces in two directions due to the combined effect of the mainstream bulk flow (Q) and the cross-flow (q); large bulk flow moves the cell along the main channel and significant enough cross-flow guides the cell into the trap. However, with too large a cross-flow, additional cells can be forced to pile onto the already-occupied trap, reducing single-cell trapping efficiency. By optimizing the fluidic resistance of the cross-flow channel with respect to the resistance of the delivery channel, conditions for trapping a single cell in a single trap can be met.

The present trapping mechanism relies on diverging flow from a main channel, wherein the bypass channel is formed by a series of parallel traps so that traps can be incorporated at a higher density; additionally, the array format ensures identical flowrates throughout the entire chamber. If the cross-flow channel has significantly higher hydrodynamic resistance than that of the main delivery channel, Q/q stays relatively constant throughout the large array, ensuring Q/q at each trap is in a proper range for trapping single cells.

Figure 9:
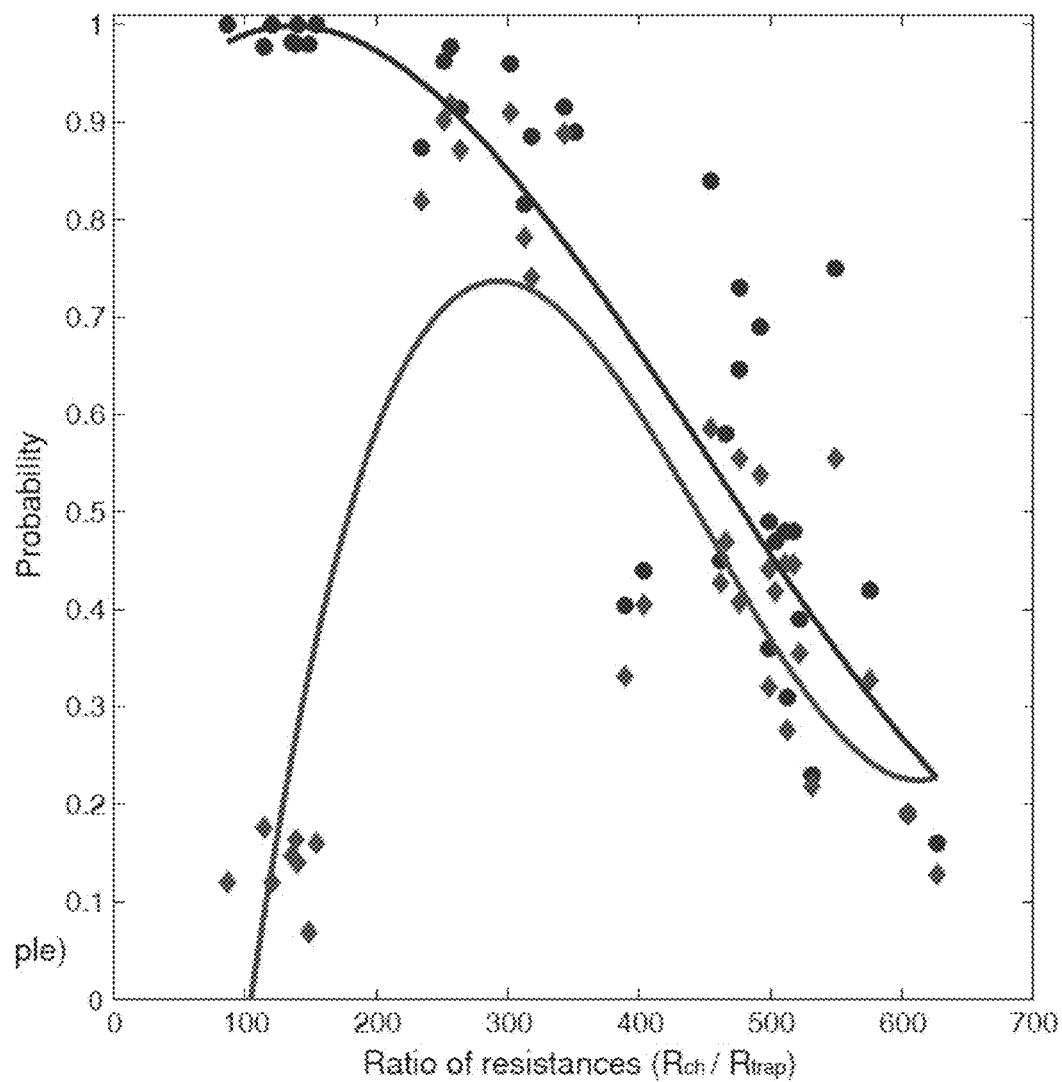
Figure 10:
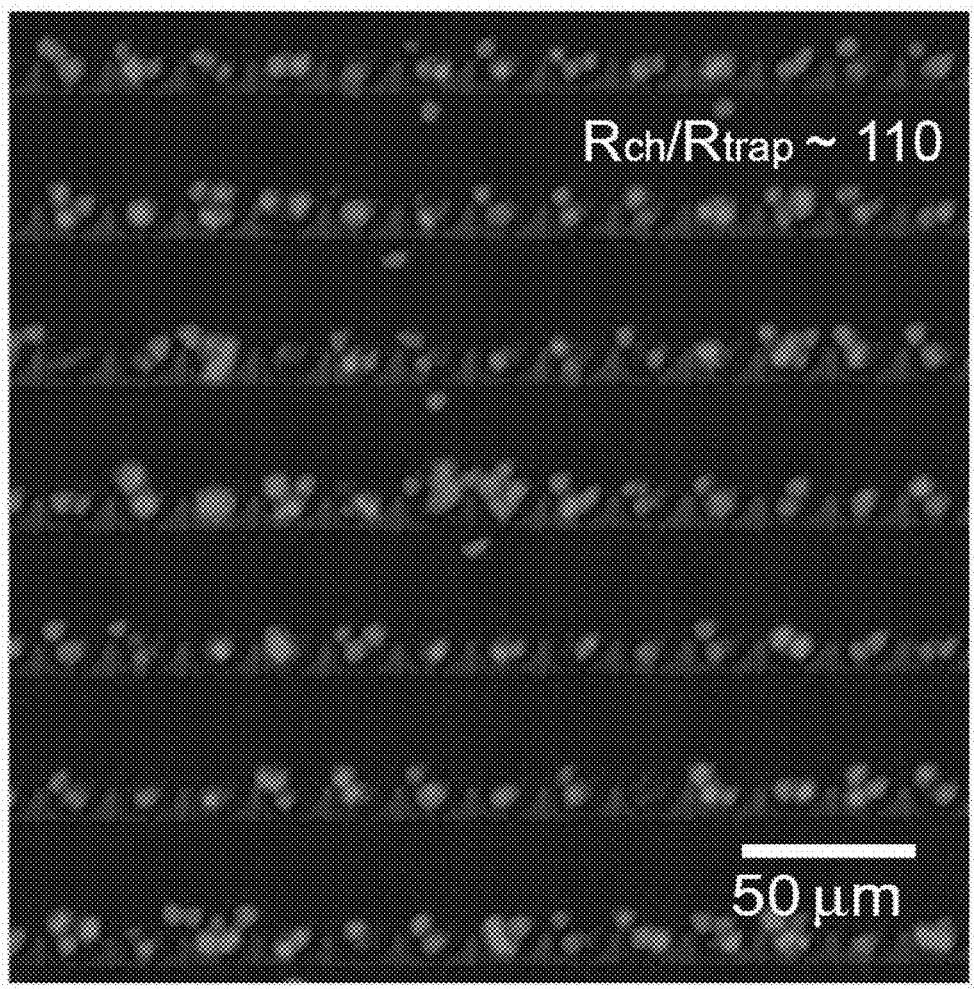
Figure 11:
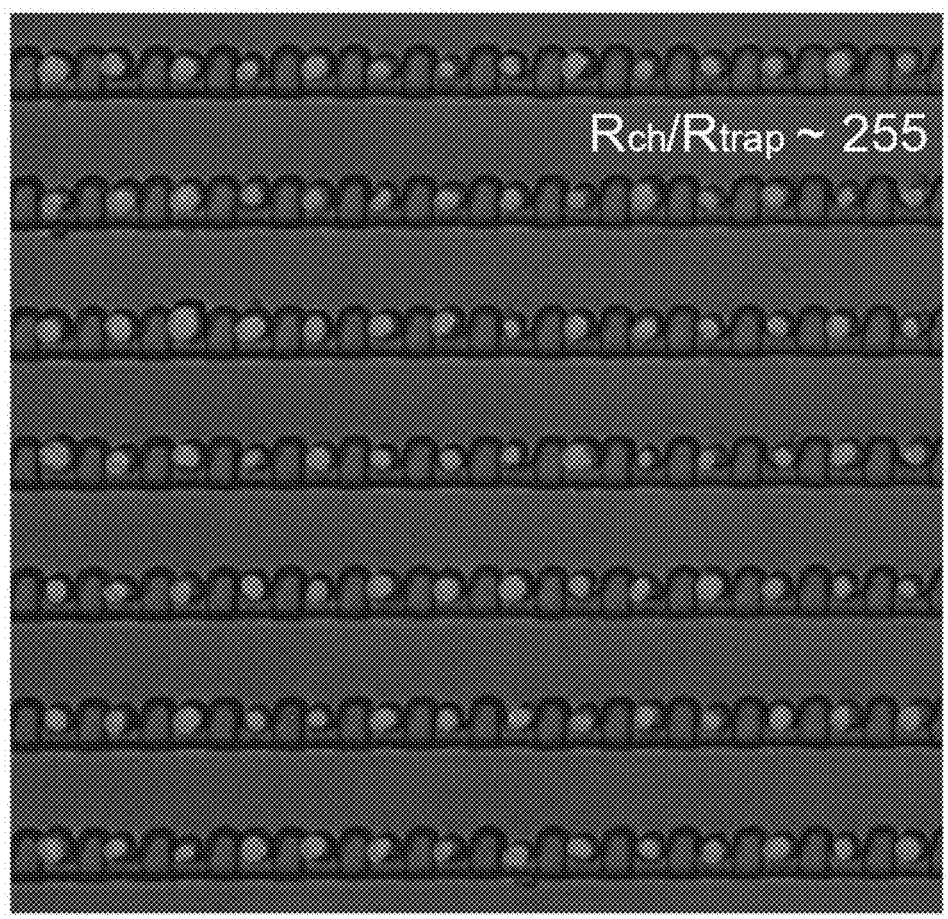
Figure 12:
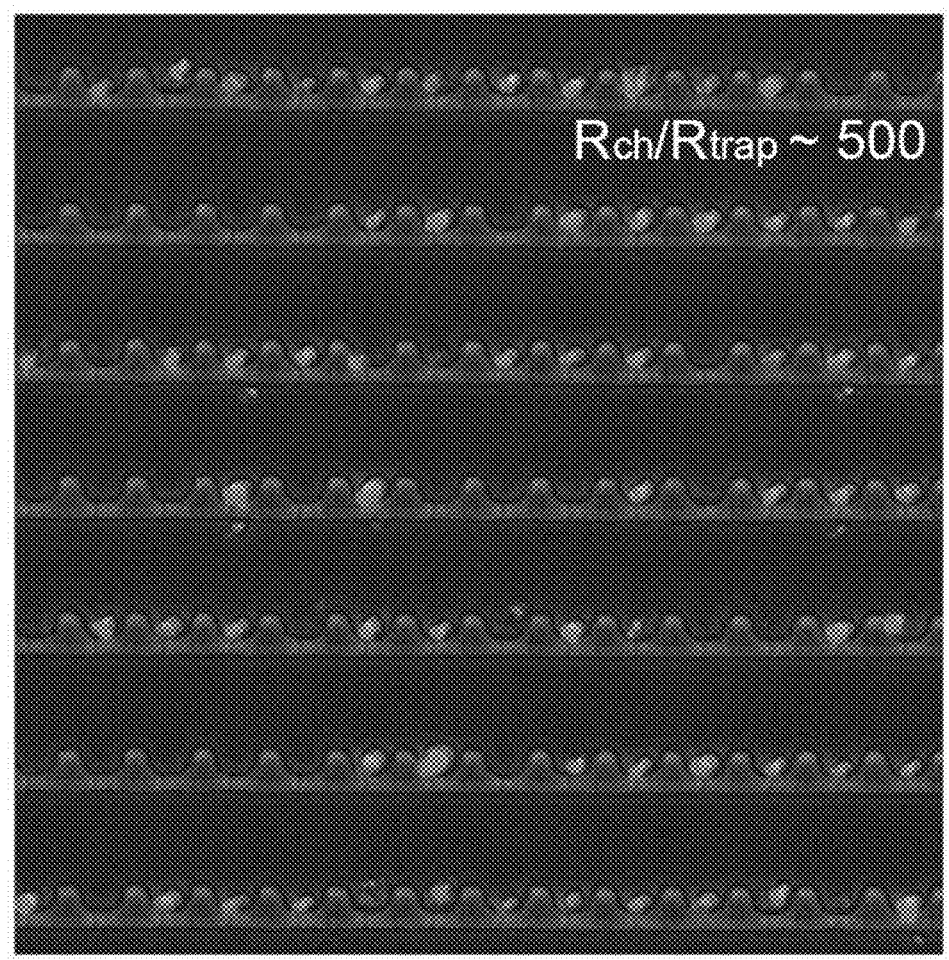

By varying the length (L), width (w), and depth ($h_{gap}$) of the trapping area and the overall depth of the main channel ($h_{mc}$) (FIG. 8), it was empirically determined that the optimal geometry for trapping Jurkat cells was 9±1 µm of diameter (FIG. 9). FIG. 9 presents the experimentally-determined probability for a trap to be filled (circles) as well as the probability for single-cell occupancy (diamonds). A low resistance ratio results in all traps being occupied, at the cost of having multiple cells per trap (FIG. 10). For high resistance ratios, the flow going through the trap is not sufficient for optimal loading, resulting in very few traps being occupied. But when occupied, only one cell is present (FIG. 12). At an optimal ratio, 93±2% of the traps are occupied with 94±1% of the occupied traps having with a single cell trapped (FIG. 11).

Using the same optimized device, the present invention was able to trap efficiently various cell types (e.g. primary T cells and Mouse Embryonic Stem Cells size varying from 8 to 20 μm), suggesting that the optimal resistance ratio is conserved in this size range. In addition, loading efficiency is independent on the initial cell concentration—cell concentration only affects loading time with high concentration loading faster. Using 10,000 cells at $5 \times 10^6$ cells $mL^{-1}$, full loading of a chamber takes less than one minute at a flow rate of 1 $\mu L \cdot hr^{-1}$. At lower flow rates, loading time is longer and cells tend to settle in the inlet reservoir. For flow rates above 6 $\mu L \cdot hr^{-1}$, cells experience high shear stress and sometimes "squeeze" through the 1.8 μm deep shallow channel, but the time-saving is not significant, so in normal use of the present invention, a flow rate of 1-2 $\mu L \cdot hr^{-1}$ was selected. An additional benefit of the present trap array design is the sequential capture of incoming cells, preventing undesirable cell loss. Of a small number of cells (e.g. 100 cells) entering the cell trap chamber, all cells will be effectively captured. This could be especially useful for precious sample capturing where the tolerance of cell loss is very low.

On-Chip Microscopy and Cell Study

Figure 13:
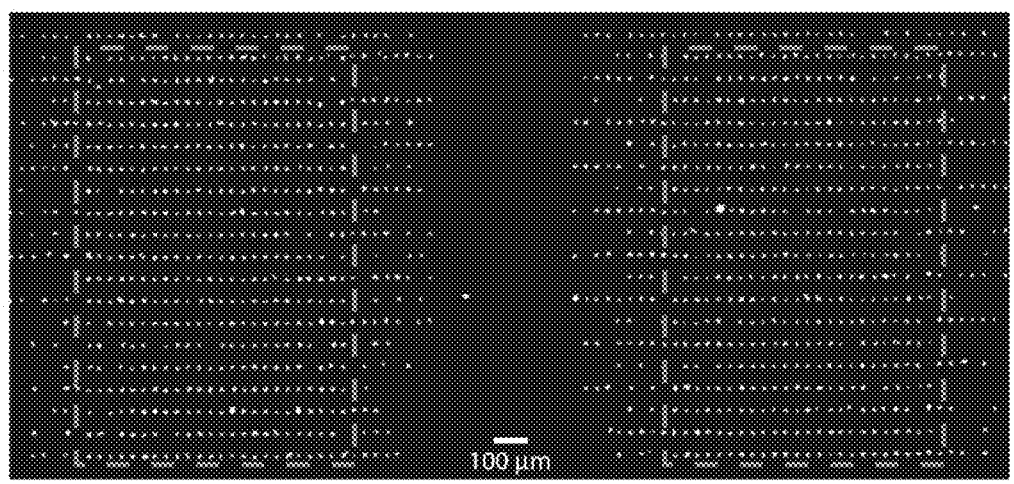
FIGS. 13-15 illustrate using an array chip for high resolution imaging of cellular features and activities according to exemplary embodiments of the present invention, where.
Figure 14:
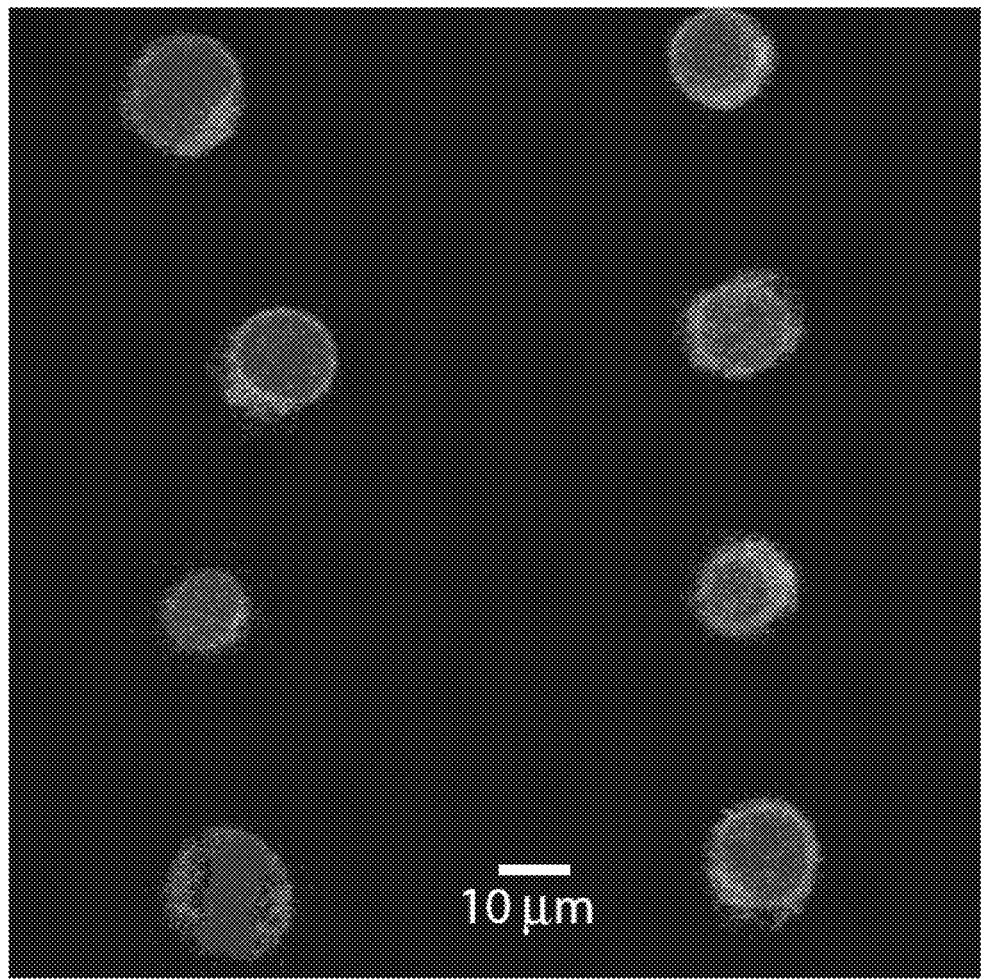
Figure 15:
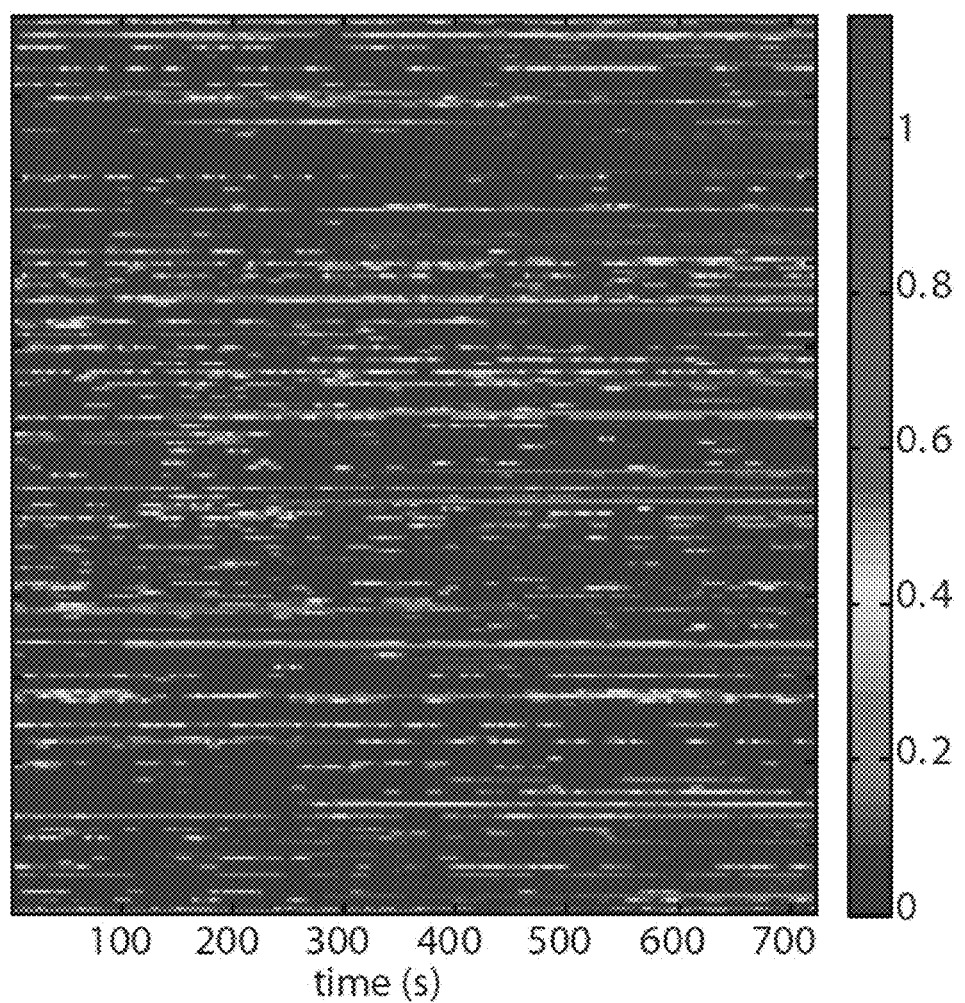
Figure 16:
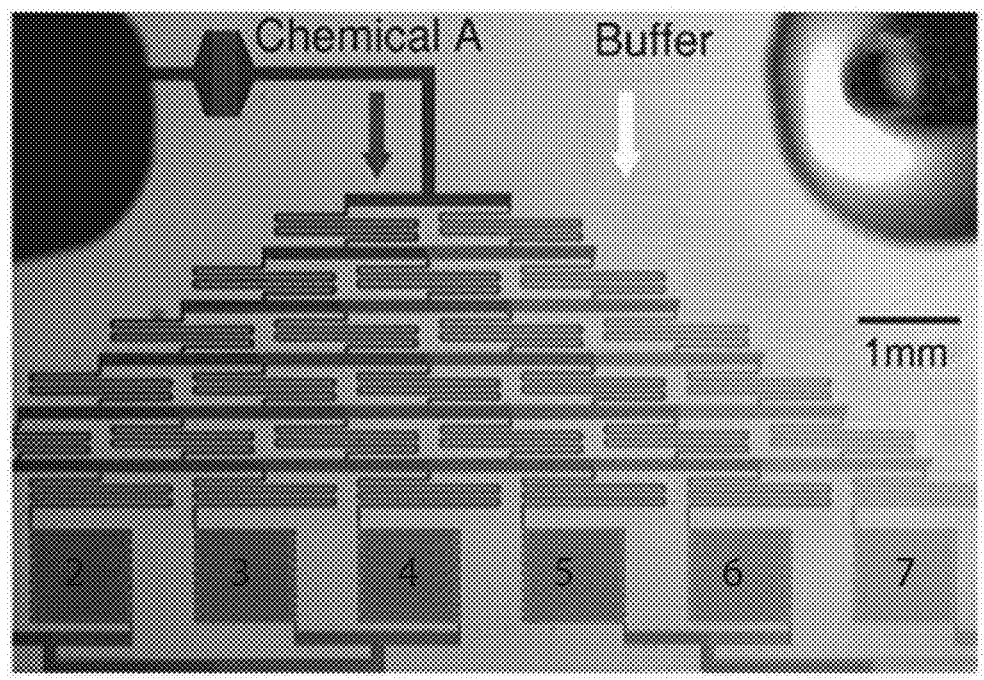
FIGS. 16-19 illustrate calcium dynamics in response to ionomycin stimulation of multiple cells tracked on chip according to exemplary embodiments of the present invention, where.

The present microfluidic platform can successfully capture and immobilize both fixed and live cells (FIGS. 13-15). To ensure trapping and perfusion rates do not induce undesirable shear stress for long-term studies, viability study on chip were performed. Jurkat cells were loaded into the chip and perfused with medium for up to 24 hours in a micro-controlled chamber. After 24 hours, 94% of Jurkat cells were still viable by live-dead stain, comparable to conventional cell culture techniques in flasks. Viability was also observed to be uniform throughout the trap array chamber, suggesting the absence of high shear stress zones in the chamber and the compatibility of the chip with long-term dynamic studies.

Another advantage of the present invention is that the high trap density allows for imaging large number of cells. For very bright signals, such as a DNA stain or calcium staining with Fluo3, low NA (low magnification) objectives can be used, and up to 800 single cells can be monitored in a field of view (FIG. 13). In a typical flow cytometry experiment, 1,000 to 10,000 data points are collected. However, these 1,000 data points correspond to 1,000 different individual cells. With the present chip and 1,000 cells, 1,000 data points were collected per time point therefore increasing the experimental throughput and reaching similar statistical significance as flow cytometry.

The present microfluidic chip is also compatible with immunostaining. Fixation, permeabilization, immunostaining and necessary wash steps can be performed on chip following standard protocol after cells are loaded into the traps. It is also possible to capture already immunostained cells, although the chances of having multiple cells per trap increase due to the increased probability of adhesion of fixed cells to each other or to the device. FIG. 14 presents Jurkat cells immunostained off chip for calnexin (endoplasmic reticulum), profilin-1 (cytoplasmic cytoskeletal protein) and Hoechst (nucleus) and imaged by confocal microscopy. Cells trapped in microwells are not always compatible with high magnification imaging due to the depth of the substrate forming the wells.

In contrast, in the present chip, cells are always located next to the coverslip, enabling high spatial resolution imaging of a few single cells at high magnification (FIG. 14). Because the cells are also at known locations on the chip in an arrayed format, thousands of cells can be imaged in one single device repeatedly.

One advantage over flow cytometry is that the present microfluidic chip coupled with real-time microscopy allows the tracking of dynamic behavior of hundreds of cells and monitoring temporal changes within single cells, which cannot be measured by flow cytometry. As a proof of concept, live cell imaging of intracellular calcium concentration in Jurkat cells was performed (FIG. 15). Two hundred trapped cells in a single chamber, loaded with a fluorescent intracellular dye specific for unbound calcium, were imaged every three seconds for duration of 15 minutes. The heat map presented in FIG. 15 highlights heterogeneity in behaviors of individual clonal cells. About 25% of these cells exhibited calcium oscillations under resting conditions, and removal of extracellular calcium abolished the oscillations in all of these cells. The oscillations are asynchronous and may arise from random fluctuations in ER calcium channels clustering rather than controlled periodic homeostatic behavior.

Figure 17:
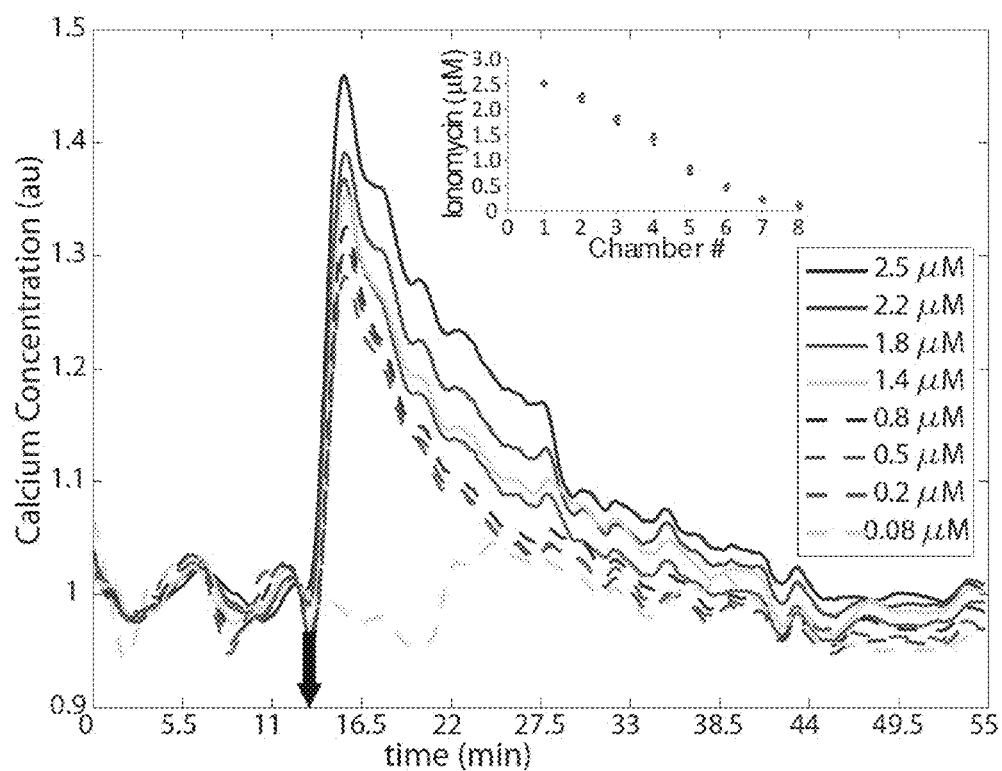
Figure 18:
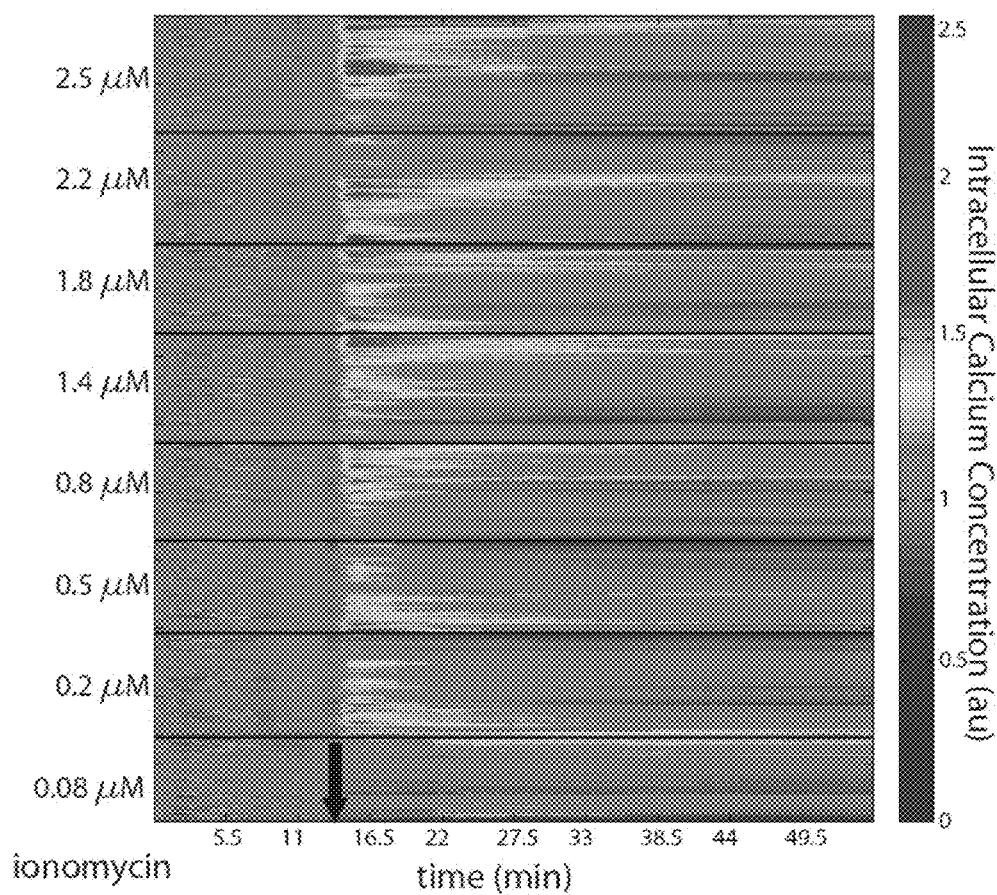
Figure 19:
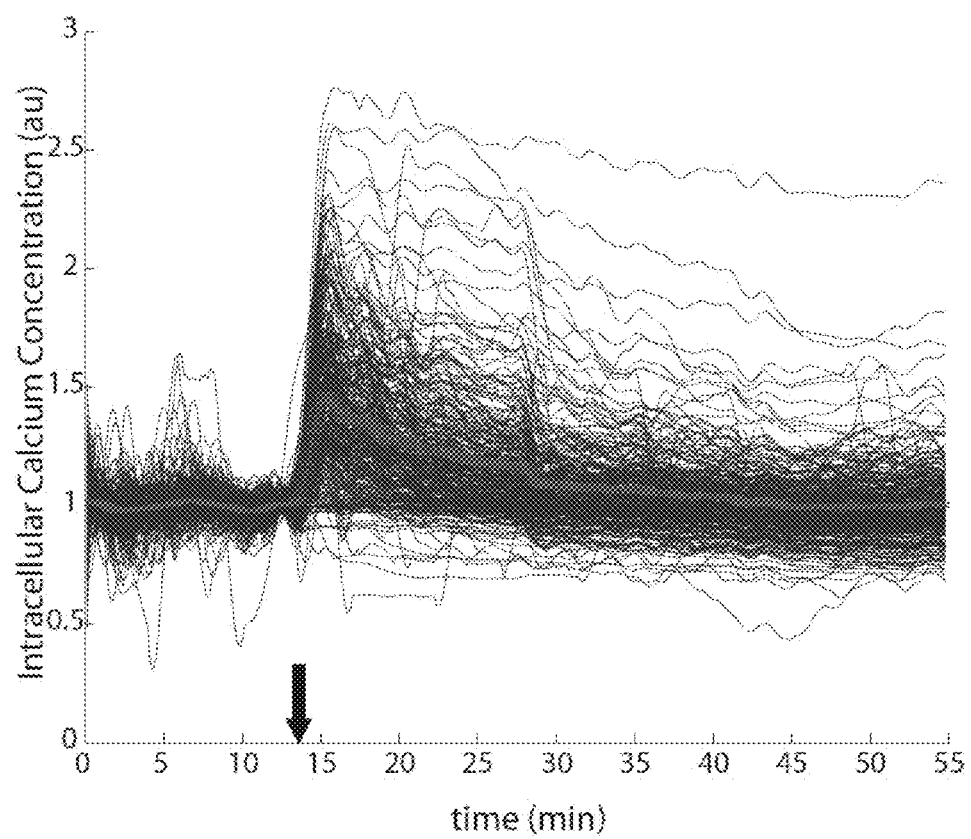

The present trap arrays can also be easily integrated with upstream microfluidic components capable of multiplexing experiments, where cells can be exposed to different extracellular conditions on a single chip. To demonstrate this capability, a cell trap chamber was coupled with a linear serial dilution generator to expose each chamber to a different concentration of the stimulus. By fluorescence measurement, the gradient of concentration was observed to be linear and not disturbed by the high resistance of the loaded cell traps (FIG. 17, inset). After loading cells containing Fluo-3, more than 1,000 individual cells were monitored for an hour after the addition of different concentrations of the calcium ionophore ionomycin. Ionomycin increases intracellular calcium via mobilization of both extracellular and intracellular calcium stores in T cells. As expected, increased concentration of stimulus lead to increased average intracellular calcium concentration (FIG. 17). Interestingly, when individual cells are monitored, it appears that only a fraction of the cell population are responding to the stimulus (FIGS. 18-19), and the fraction of responding cells increases linearly with increasing concentration of stimulus ($R^2$=0.88) as shown by unsupervised clustering for each chamber in FIG. 18 and TABLE 1; however, cell response was not correlated to position in the array nor to the presence of oscillations prior to stimulation. This observation of partial calcium response of a cell population to external stimulus is not unprecedented; as reported for clonal human embryonic kidney 293 cells when challenged with caffeine, only 40% respond with an elevation in intracellular calcium due to in endogenous protein expression levels. Cellular response in terms of amplitude and duration of cytoplasmic calcium influx were not dependent on their respective position in the array. In addition, cells in the lower rows receive the stimulus with minimal delay compared to cells in upper rows of the array, which suggests a homogenous stimulus delivery throughout the array.

A similar experiment was performed using flow cytometry as a technique to measure calcium kinetics of Jurkat cell in response to 2.5 μM of ionomycin. The average response of cells was comparable for both techniques, with a similar standard deviation due to population noise. To get 15 minutes of calcium dynamics, the present chip only requires 300 cells as opposed 86,200 cells with a kinetic read with flow cytometry. Moreover, flow cytometry does not enable one to monitor the early kinetics after addition of the stimulus (20 seconds), and because fluctuations within one cell cannot be quantified, flow cytometry cannot discriminate between oscillating and non-oscillating cells. In addition, discrimination between responding and non responding cells at different time points is facilitated by the present chip.

TABLE 1

Calcium response to various ionomycin concentrations

| Chamber Number | Number Of Tracked Cells | Ionomycin Conc. (µM) | % Responding Cells |
| --- | --- | --- | --- |
| 1 | 342 | 2.5 | 44% |
| 2 | 328 | 2.2 | 33.2% |
| 3 | 263 | 1.8 | 31.9% |
| 4 | 322 | 1.4 | 31.1% |
| 5 | 287 | 0.8 | 25.4% |
| 6 | 273 | 0.5 | 19.1% |
| 7 | 306 | 0.2 | 17% |
| 8 | 250 | 0.08 | 4% |

A Microfluidic Array for Large-Scale Ordering and Orientation of Embryos

Introduction

Spatial control of cell differentiation in embryos can be provided by the graded distribution of morphogens, chemical signals that act as dose-dependent regulators of gene expression. Quantitative analysis of developmental systems controlled by morphogens requires information about both the regulatory regions of genes comprising the network and the spatial distribution of patterning signals. Some of the first morphogen gradients were identified in the Drosophila embryo, where the dorsoventral (DV) axis of the embryo is patterned by the nuclear localization gradient of Dorsal (Dl), an NF-κB transcription factor, which subdivides the embryo into three germ layers. The regions exposed to high, medium, and low levels of Dl, respectively, contribute to the formation of the mesoderm, the nervous system, and the skin of the embryo.

The DV patterning system in Drosophila is arguably one of the best understood systems with regard to its sequence-specific transcriptional regulation. However, the information about the distribution of patterning signals is currently lacking, mainly due to the technical difficulties associated with the imaging the spatial distribution of proteins and transcripts along the DV axis of the embryo. When imaged on a regular microscope slide, embryos are oriented with their major axis parallel to the cover slip, and their DV orientation is essentially random. Since only a small fraction of embryos can be used for quantitative imaging, previous analyses of signals in the DV system relied on data collected from ~10 embryos.

To enable high-throughput analysis of the DV patterning signals, the present invention can comprise an array in which hundreds of embryos are oriented vertically in a matter of a few minutes. Such "end-on" orientation allows for the entire DV axis data to be collected from multiple embryos easily. Previously, end-on imaging has been possible only for very small numbers of embryos, which had to be individually and manually placed into an upright position. With an easy-to-use META device, a fluid carrying hundreds of embryos is injected into the device using a simple pressure source. In a few minutes, the fluid flow directs the embryos into the traps, and the device with the loaded embryos can be mounted onto a microscope stage or stored for future use.

The present invention can be used to quantify morphogen gradients in fixed embryos and to monitor nuclear divisions in live embryos. The design enables high-throughput analysis of the dorsoventral patterning system at the level of the inductive cues and their signaling and transcriptional targets in the wild type and mutant backgrounds. A large number of analyzed embryos allowed the statistical analyzation of the patterning signals in fixed embryos. In particular, the present invention resolved the outstanding issue regarding the spatial extent of the Dl morphogen gradient, and demonstrates how this gradient can be quantitatively compared between the wild-type and mutant backgrounds.

Figure 20:
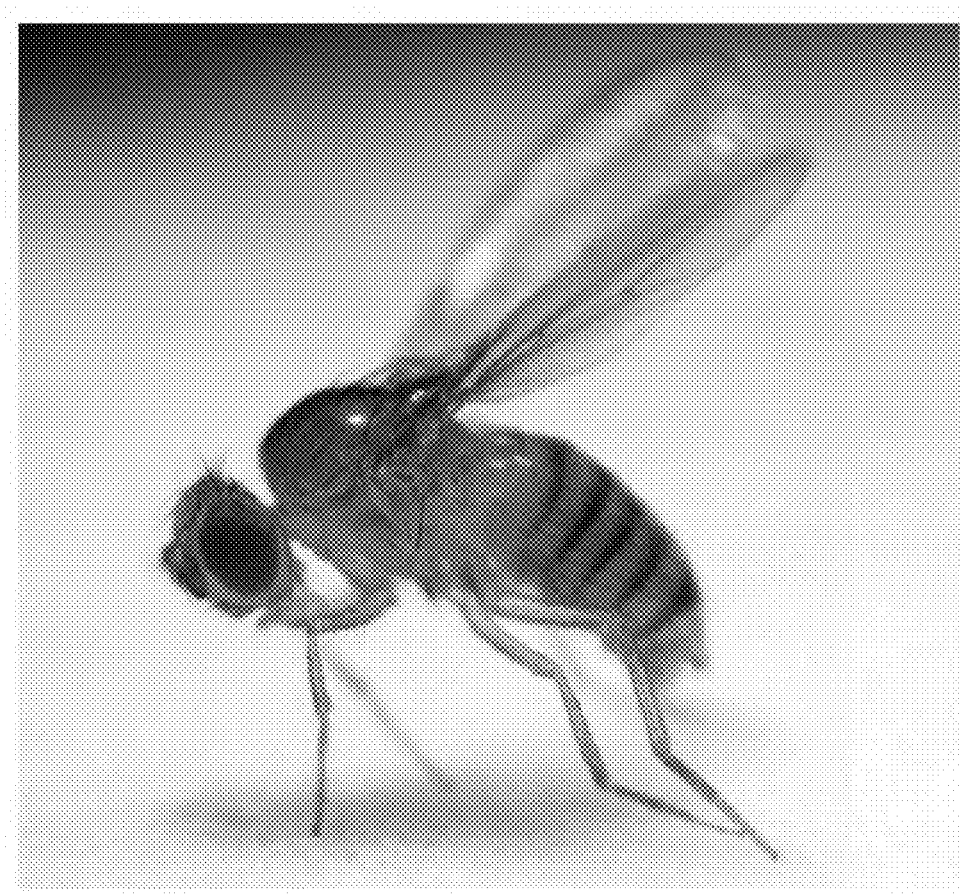
FIG. 20 is a photo of an adult *Drosophila*. The dorsoventral (DV) polarity of an adult *Drosophila* is specified in the early embryo FIG. 21 by the nuclear localization gradient of Dorsal (Dl), an NF-κB transcription factor, visualized using an anti-Dl antibody staining. The scale bar is 100 µm.
Figure 21:
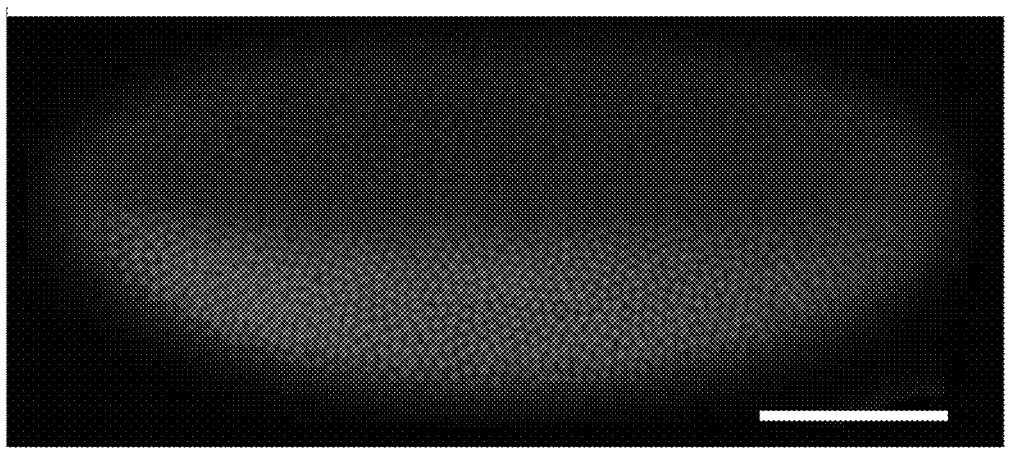

The dorsoventral (DV) polarity of the adult Drosophila (FIG. 20) is specified in the early embryo (FIG. 21), by the nuclear localization gradient of Dorsal (Dl), an NF-κB transcription factor, visualized using an anti-Dl antibody staining. Both images are oriented with anterior left and dorsal side up as shown by the two arrows on the right. The scale bar is 100 µm.

Results

Design of META Devices

The present META comprises a one-layer microfluidic device fabricated from polydimethylsiloxane (PDMS), an optically transparent elastomer widely used in biological microfluidics. In order to allow for imaging of a large number of embryos, the array needs to be compact, i.e. having traps that are densely packed, which is an engineering challenge. Conventional approaches using hydrodynamics for cell trapping typically does not achieve such high packing density; this is mostly due to the requirement of proper balancing of flow resistance, resulting in rather large space between neighboring traps. The mechanism used in the present design, in contrast, does not rely on resistance change upon the occupation of traps, and therefore allows for densely arraying ~700 traps in the space of a microscope slide (FIGS. 22-23).

Figure 22:
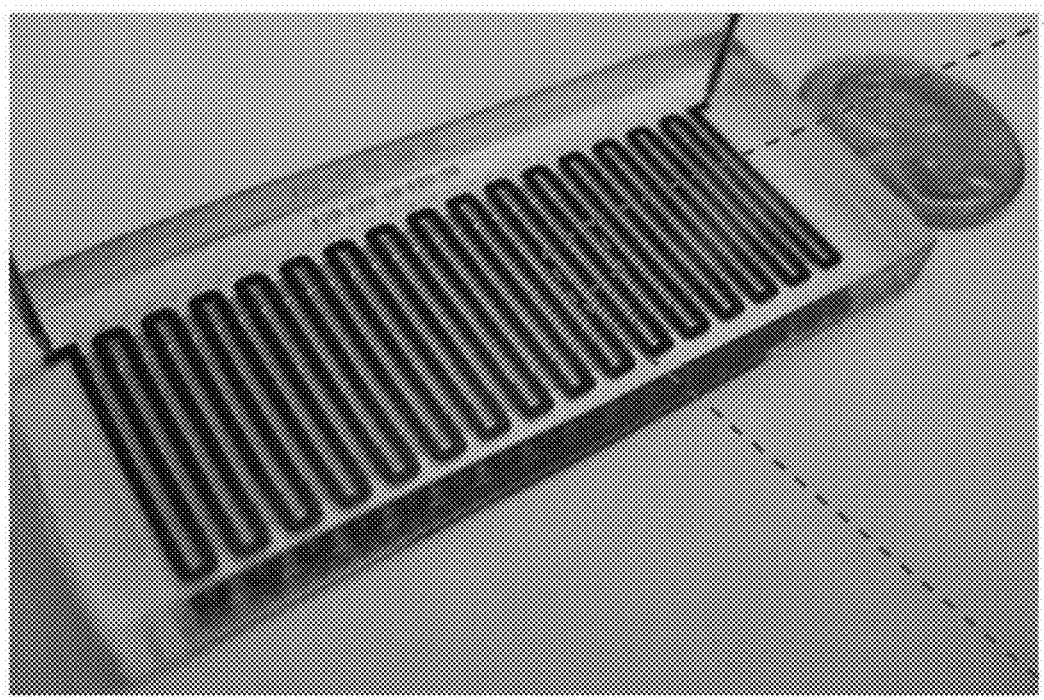
FIG. 22 is a photograph of a META design according to an exemplary embodiment of the present invention.
Figure 23:
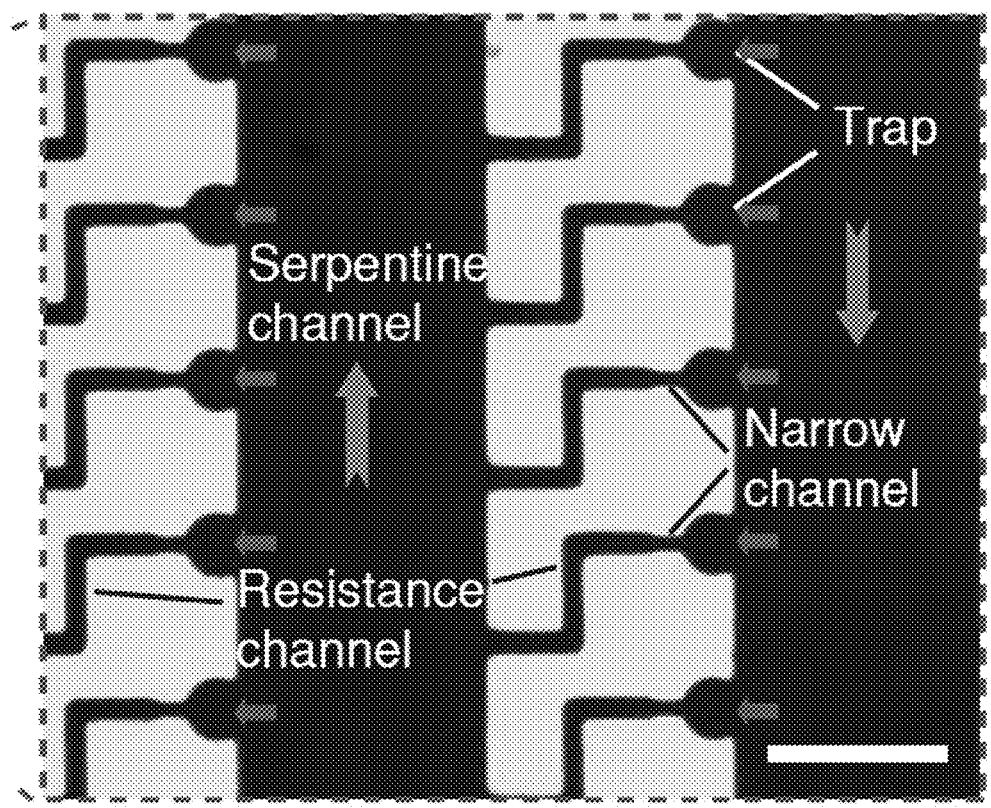
FIG. 23 is an optical micrograph of the region in the box of FIG. 22, showing array of the embryo traps. The scale bar is 500 μm.
Figure 24:
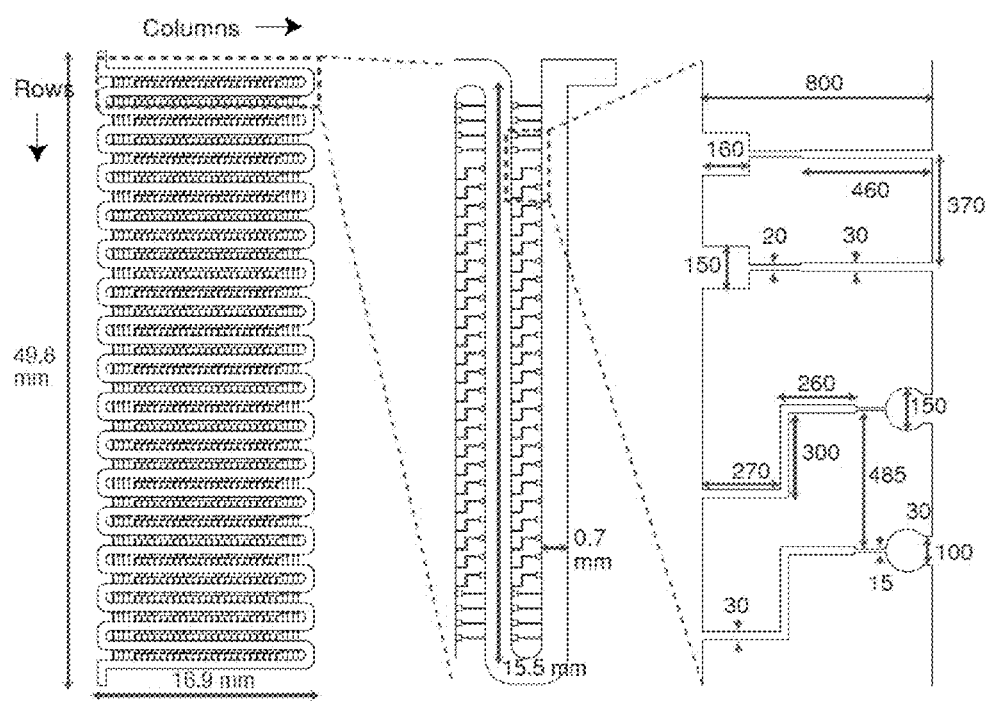
FIG. 24 are drawings and details of a META design (top view) according to an exemplary embodiment of the present invention, wherein units are in μm unless otherwise stated.
Figure 25:
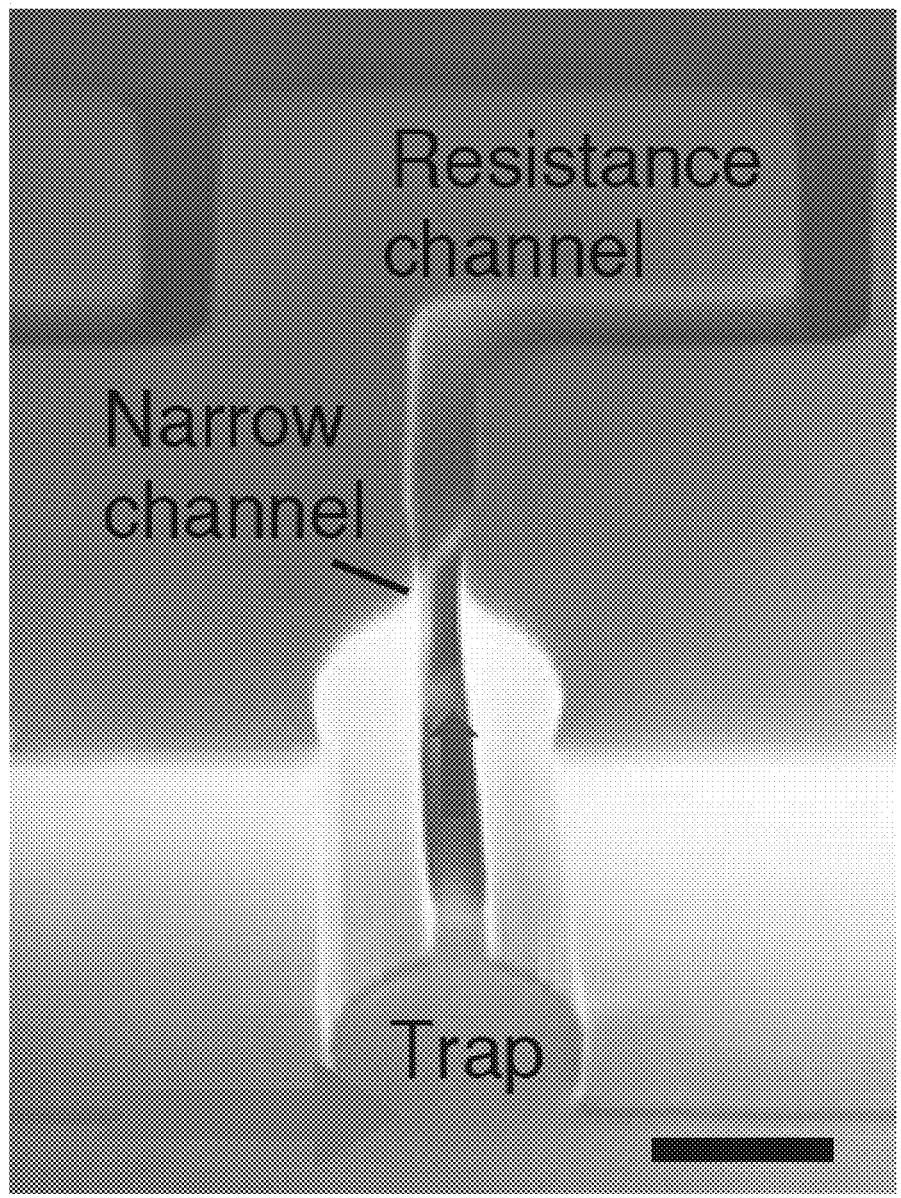
FIG. 25 is a scanning electron micrograph image showing details of a trap structure according to an exemplary embodiment of the present invention. The scale bar is 100 μm.
Figure 26:
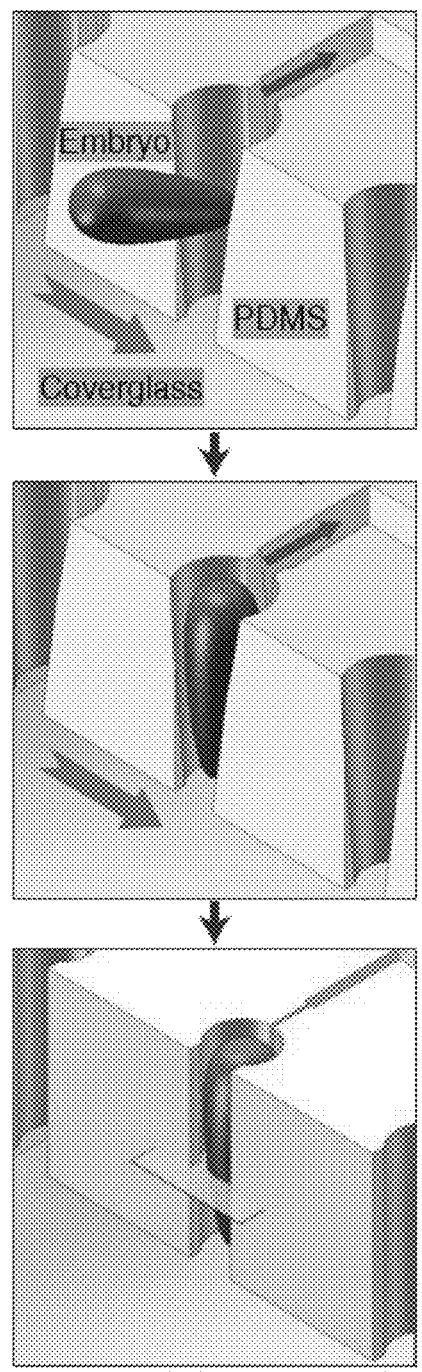
FIG. 26 are schematic diagrams showing the embryo trapping process: top, an embryo is guided into the cylindrical trap by the cross flow; middle, the flow around the embryo orients it vertically; bottom, the trap contracts after loading is finished and secures the embryo inside the trap. In color drawings, the yellow plane represents the focal plane where images are obtained.
Figure 27:
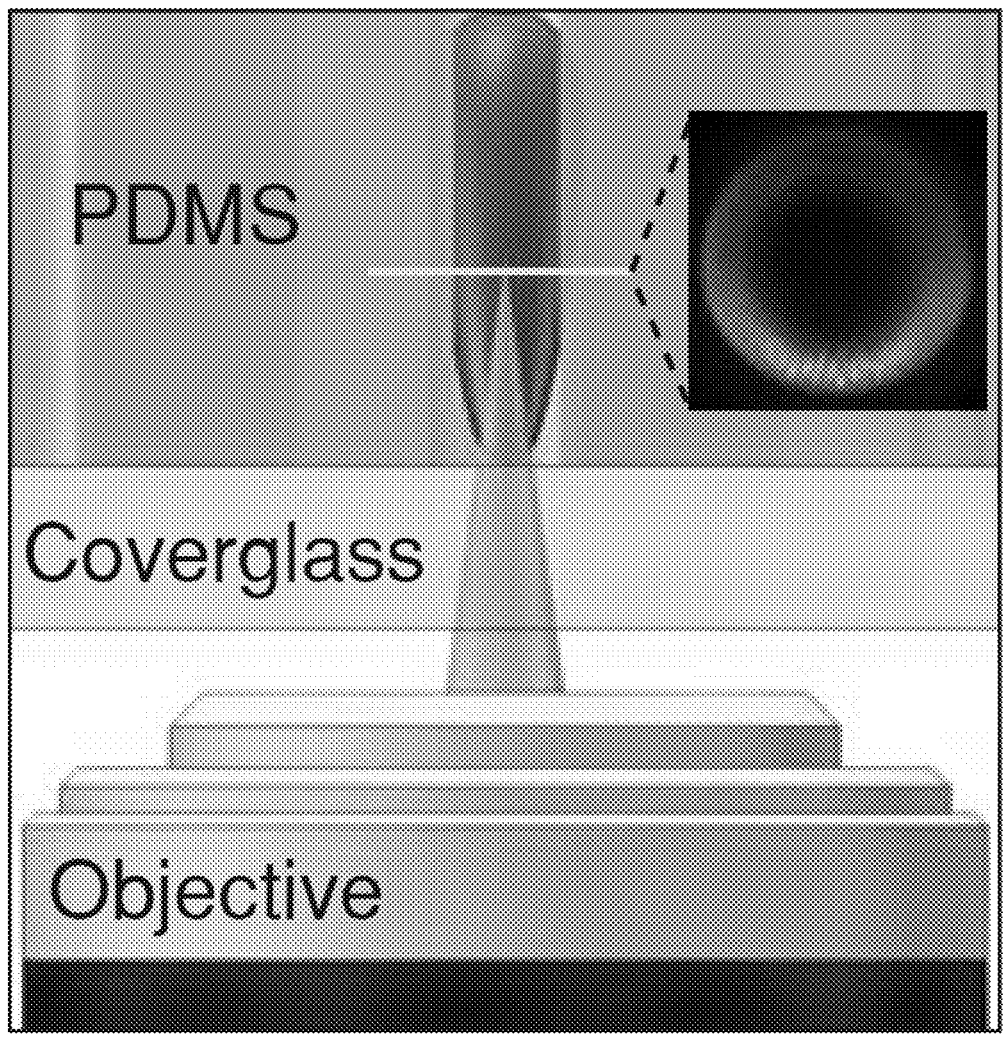
FIG. 27 is a schematic drawing showing an imaging setup. The inset is a representative confocal image of an embryo stained with Dorsal, Twist, and phosphorylated ERK/MAPK.
Figure 28:
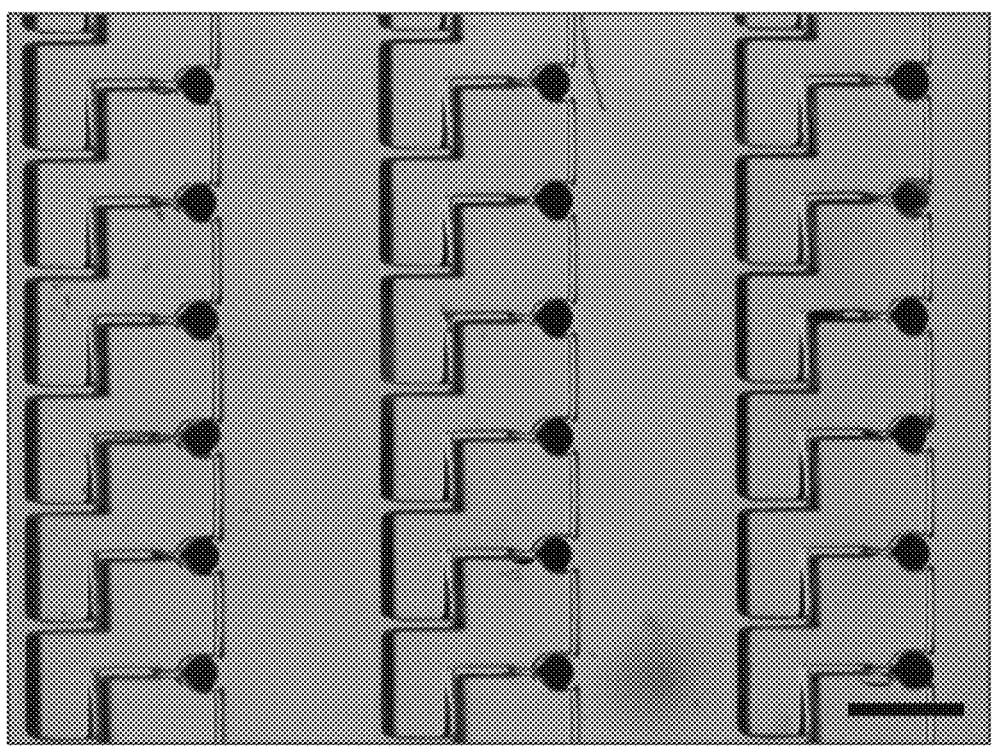
FIG. 28 is an optical image of a section of a META with embryos trapped in a packed array according to an exemplary embodiment of the present invention. The dark circular object in each trap is a successfully oriented and trapped embryo. The scale bar is 500 μm.

The present META comprises a serpentine fluid-delivery manifold and an array of cross-flow channels (FIGS. 22-24). A 700-µm wide serpentine channel can be used, which is wider than the major axis of the embryo (~500 µm). This allows embryos of any orientation to move easily through the channel. This feature is particularly important for the robustness of the handling of non-spherical objects like Drosophila embryos. Each cross-flow channel includes a truncated cylindrical trap where the embryo is located for imaging. The trap is connected to a narrowing channel and a long and narrow resistance channel (FIGS. 24-25). When an embryo approaches an empty trap, the flow through the trap guides it into the trap (FIG. 26). The shape of the trap dictates that the embryo is in an upright position for imaging (FIG. 27). Because the traps are microfabricated, the present device automatically guarantees that each embryo on every device is oriented with the dorsal-ventral plane being horizontal. Vertically oriented embryos, which appear round when viewed from the top, are then arrayed in META (FIG. 28).

Figure 30:
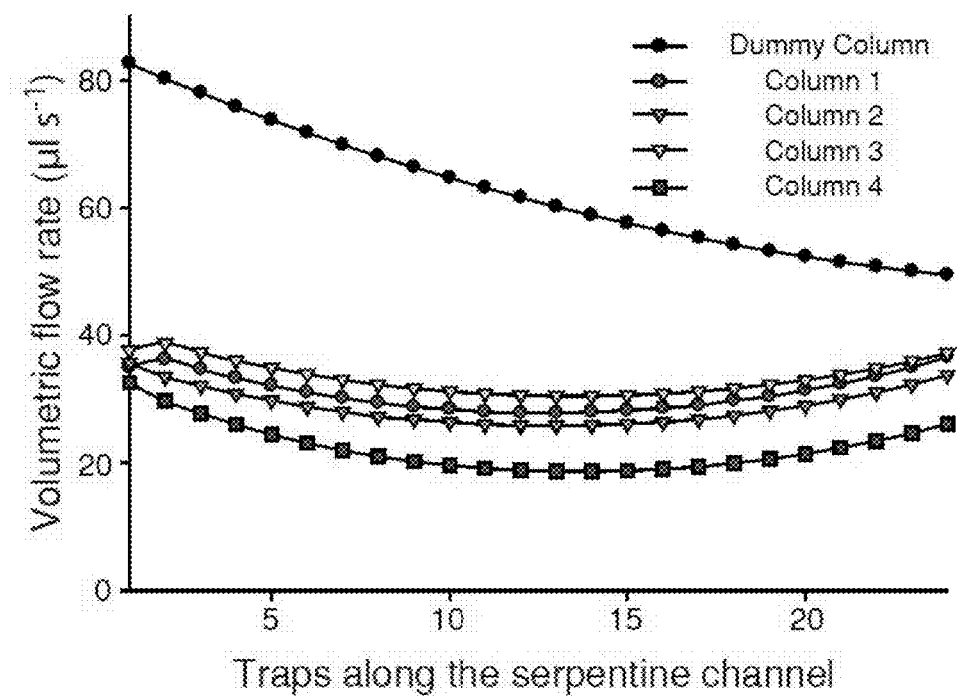
FIGS. 30 and 32-34 provide META's operating principles, including mechanisms of META's high-efficiency trapping. Dummy columns are the columns at the edge of the device.
Figure 31:
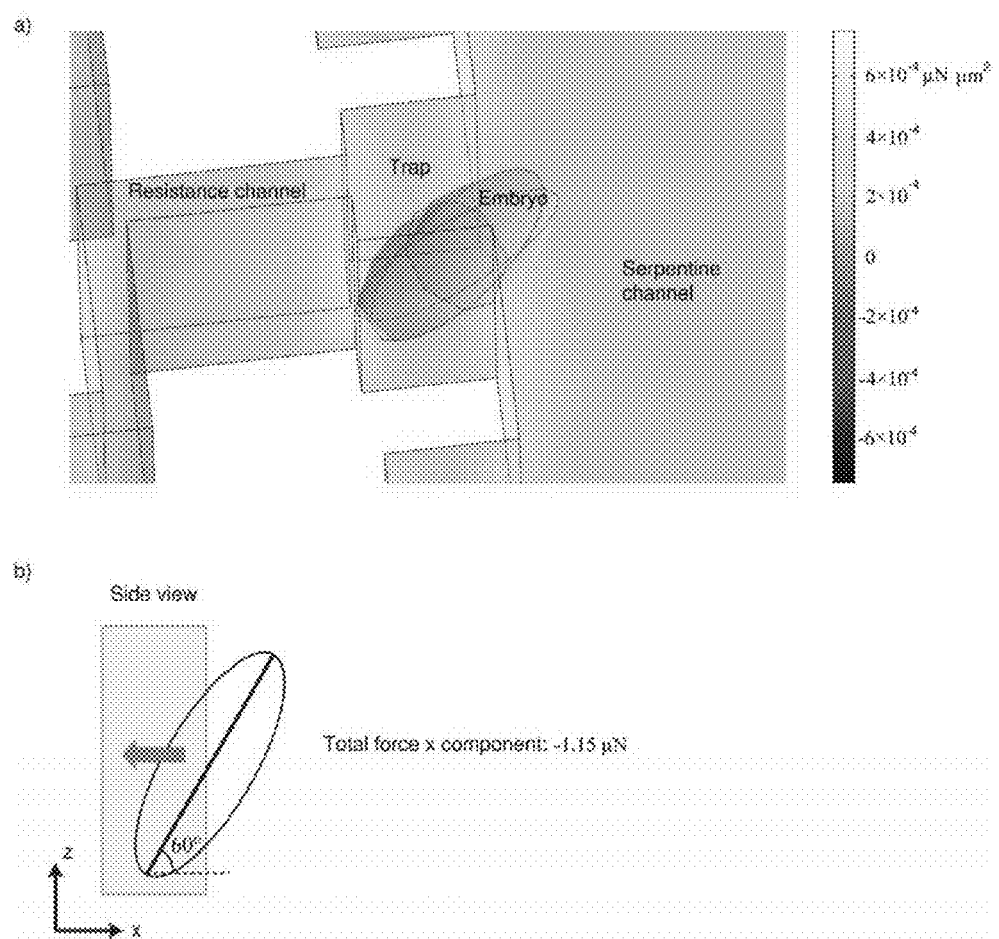
FIGS. 31(a)-(b) illustrate the mechanism of embryo flipping into a vertical orientation.

Using a computational fluid dynamics approach, the hydrodynamic resistances of the cross-flow channels was engineered. A simplified smaller array in a three-dimensional computational model (FIGS. 29(a)-(b)) demonstrates the general principle of the present design that satisfies the following criteria:

First, all the traps are exposed to similar flow rates (FIG. 30). If the flow in the entire array has large variations in different rows or columns, the trap occupancy would be severely compromised; optimal design, however, yields highly repeatable near-perfect occupancy, as shown experimentally (FIGS. 31(a)-(b)).

Figure 32:
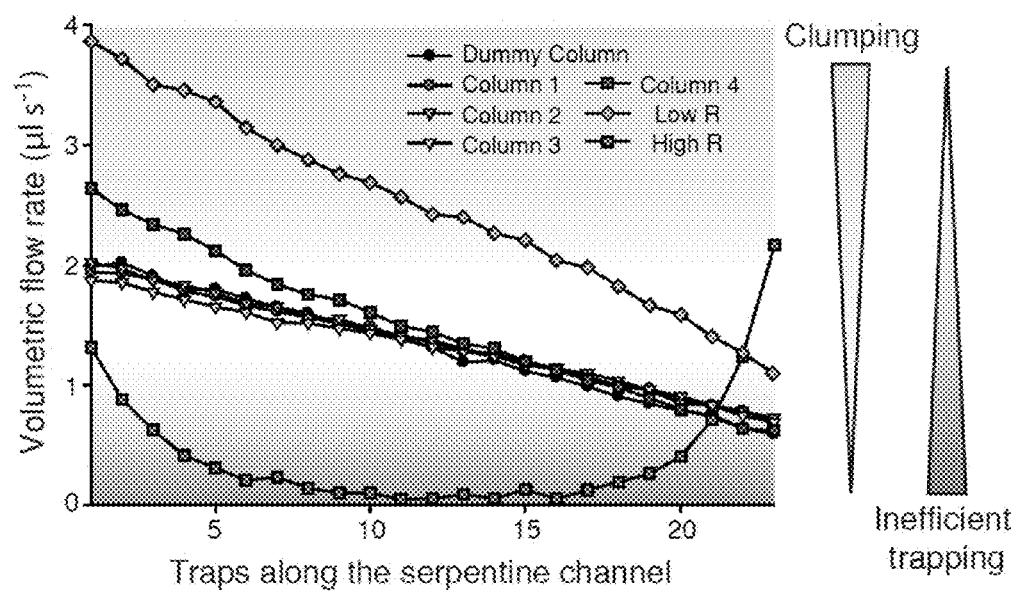

Second, the bulk of the embryo suspension flows along the serpentine manifold (comparing flow rates of FIGS. 30 and 32). The bulk flow through the main channel efficiently sweeps out extra and improperly trapped embryos. In addition, too low a cross flow through the traps prevents embryos from being introduced to the traps, resulting in inefficient trapping (blue region in FIG. 32); on the other hand, high cross flow causes embryos to accumulate near traps and clump together (yellow region in FIG. 32). From the understanding of the design space and by picking proper parameters, an optimal design of META that works well with Drosophila embryos is provided.

Figure 33:
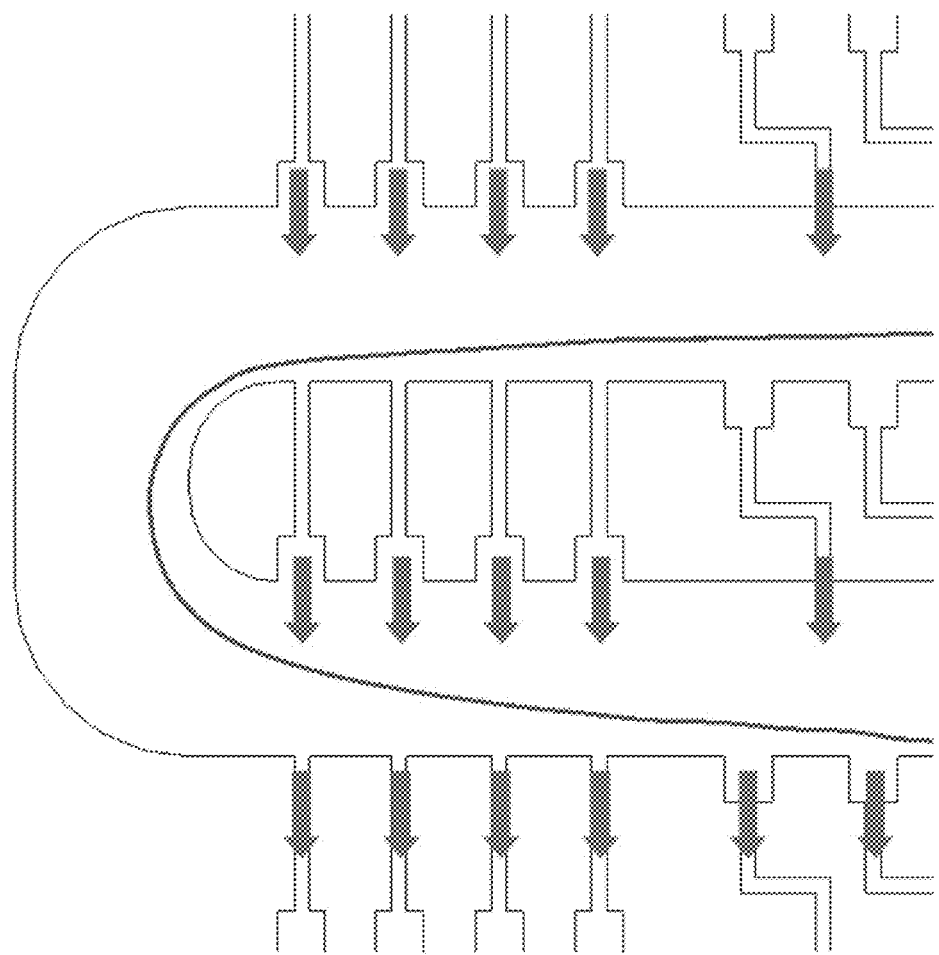
Figure 34:
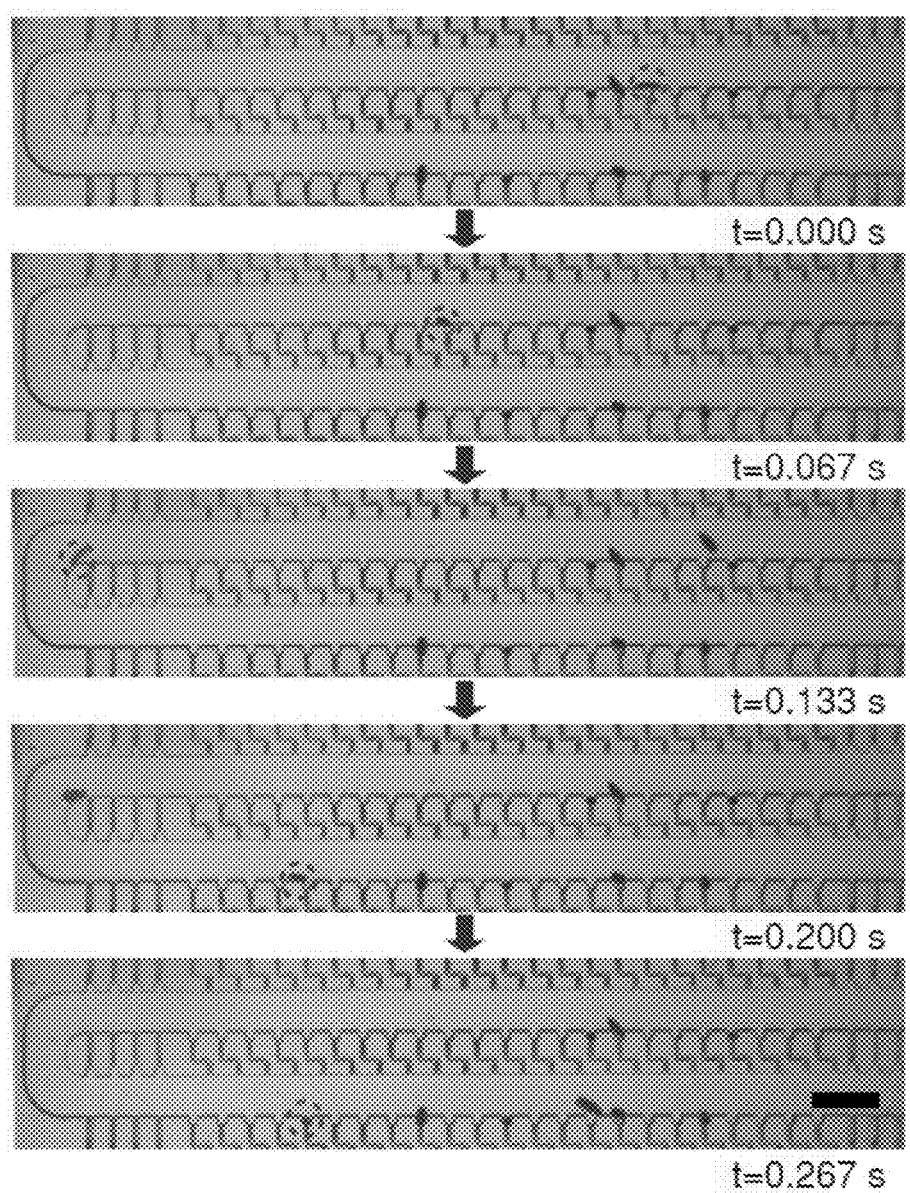

Another important mechanism for orientation of embryos in the present device is the presence of a significant Dean flow (with a Dean number greater than 100 throughout the device), an effect in which curvature of the channel induces a secondary non-axial flow. This effect is apparent in the stream-line trace in FIG. 33 and frames from an embryo loading video (FIG. 34). This hydrodynamic effect focuses the embryos towards the traps (as opposed to embryos distributing in random locations in the bulk flow), and significantly increases the frequency with which embryos contact the traps and are loaded into them. The presence of the secondary Dean flow at the bends of the channel not only greatly improves the trap occupancy, but also maximizes loading efficiency, since an embryo has many opportunities to be in contact with an empty trap. In fact, essentially every single embryo entering the device is trapped, a useful feature in studies where one has to work with small numbers of embryos in complex genetic backgrounds. The percent of traps loaded with embryos was experimentally observed to be ~90%.

Figure 35:
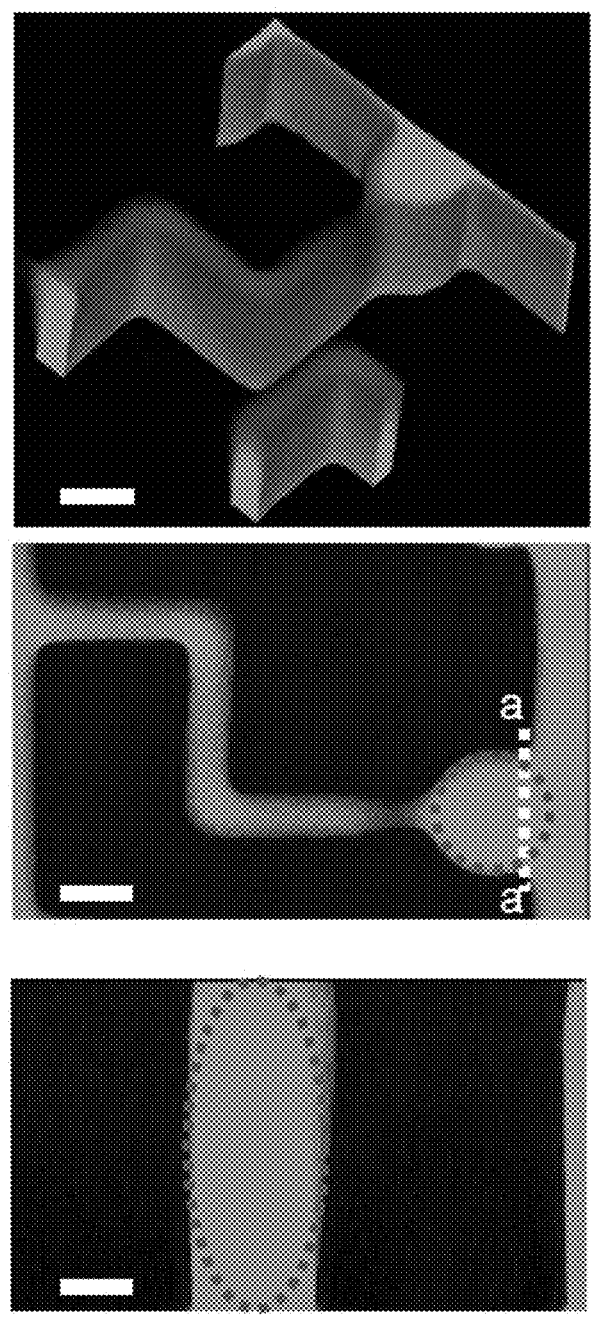
FIGS. 35-36 illustrate three-dimensional (3D) reconstructions of a trap imaged by confocal microscopy. Each trap can be expanded by positive pressure while loading, and contract in order to hold embryos in the vertical position while imaging.
Figure 36:
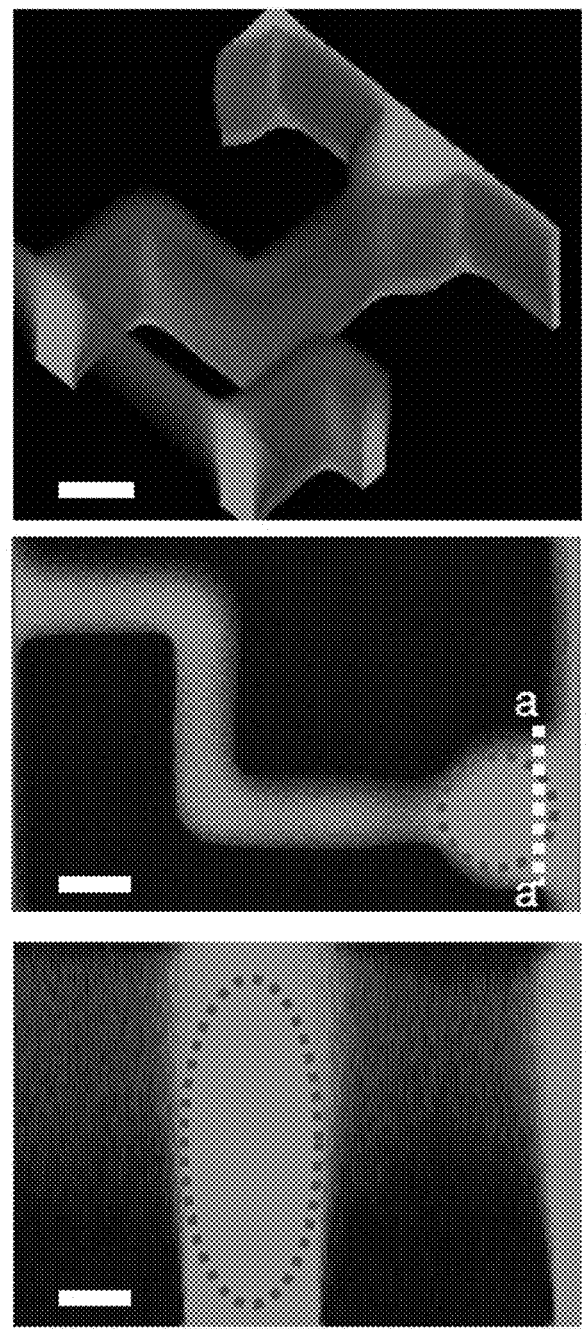
Figure 37:
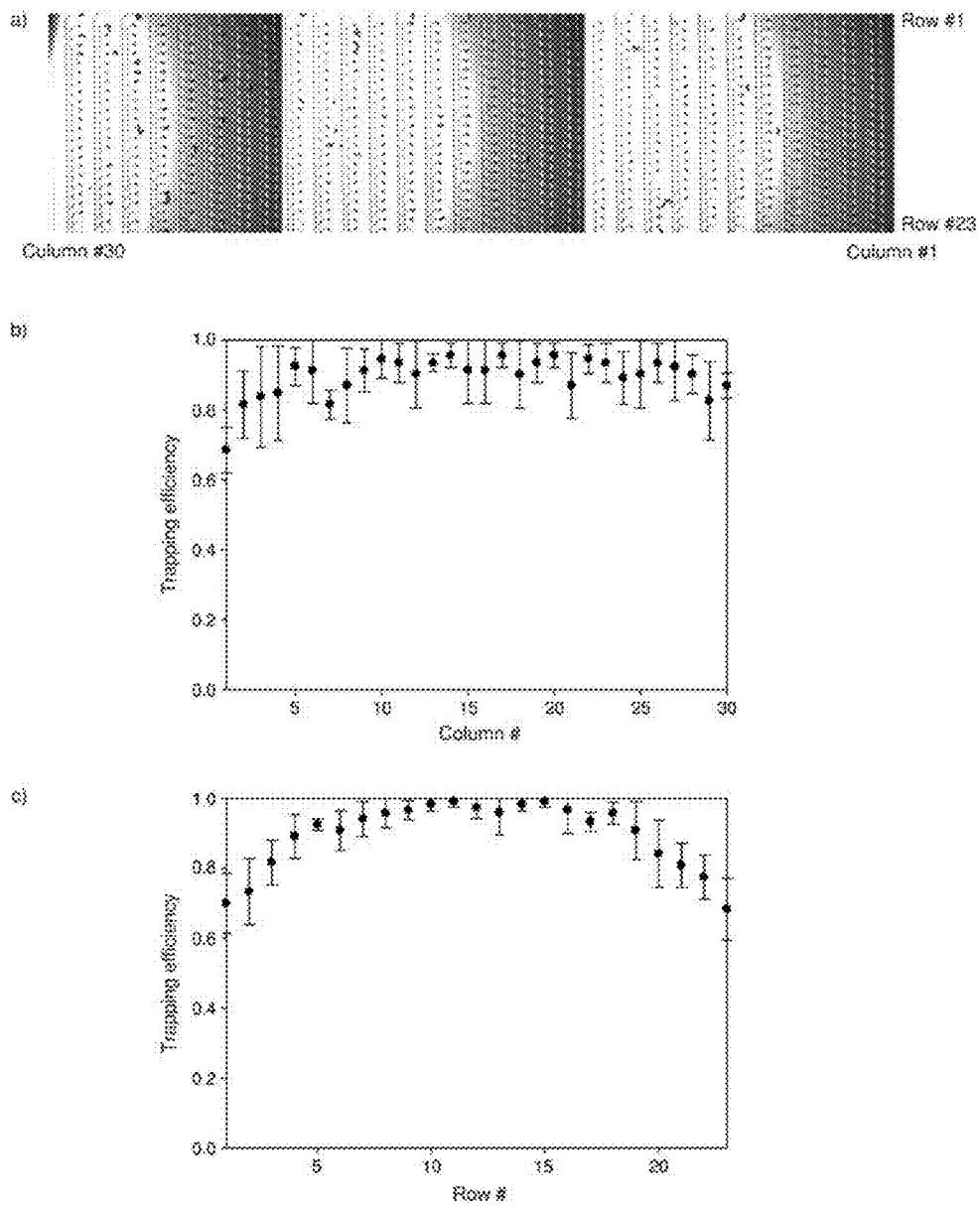

Once an embryo is in the vicinity of an empty trap, it is directed into the cylindrical traps by the cross flow. During this process, the entire device is under a slight positive pressure, and because the PDMS is an elastomer, the pressure can expand the trap opening to facilitate loading (FIG. 26 and FIGS. 35-36). Confocal characterizations of the trap behavior under different pressures (FIGS. 35-36) demonstrates that at ambient condition (0 psi), the traps have smaller openings (not enough for an embryo to be loaded or released), as compared to under 6 psi of positive pressure. When operating the device, it is connected at the outlet to a pressure-drop tube. The purpose is to raise the average pressure of the META device to ~6 psi to open the traps. The embryo suspension is then introduced into the device using a syringe driven by hand or a pressure source (e.g. compressed air).

Figure 38:
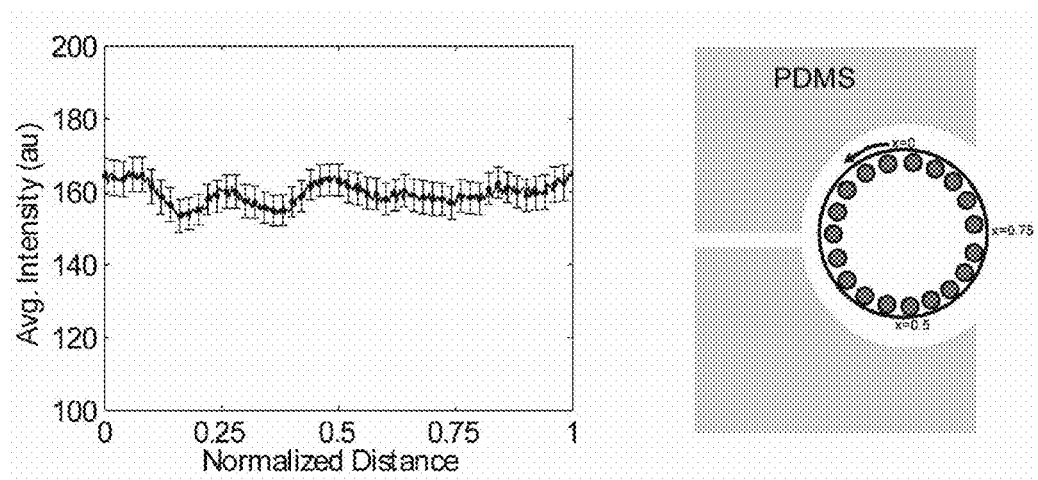
FIG. 38 shows quantifications of DAPI signals from raw images without aligning gradient in the DV axis. The schematics on the right show the definition of normalized distance. The DV axis is random in the embryos. For n=88 embryos analyzed here, an ANOVA test on the mean along the circumference (x-axis) gives P~1, demonstrating that there is no systematic bias in the illumination in the embryo.
Figure 39:
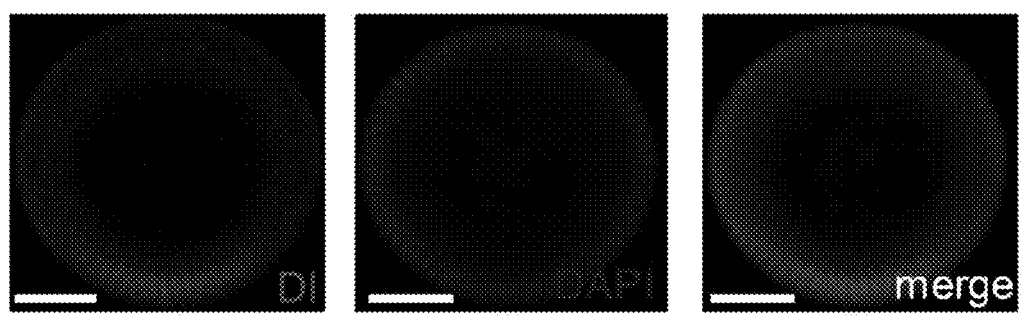
FIG. 39 includes images of the Dl and nuclei in a vertically oriented embryo.
Figure 40:
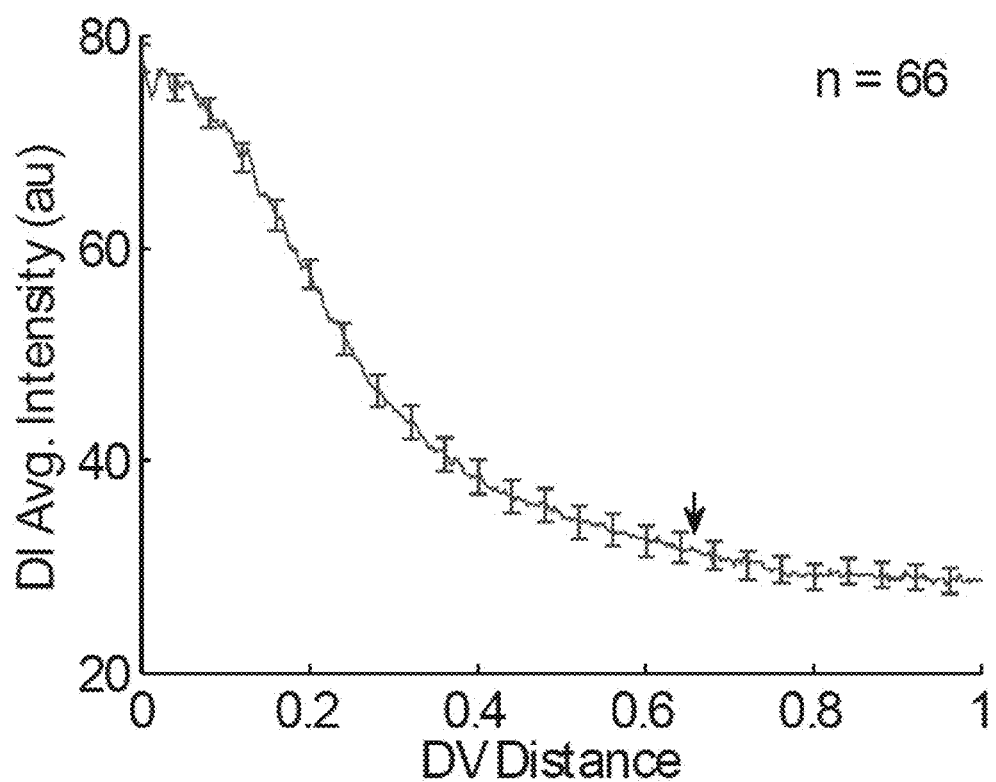
FIGS. 40-43 illustrate average gradients of nuclear Dl from four representative experiments. The gradients are shown with standard errors of the mean along the DV axis. The number of embryos analyzed in each experiment is indicated. The arrows denote the DV position beyond which the spatial pattern of nuclear Dl can be considered flat, based on a pair-wise statistical test of the differences of the mean values at a given position and the dorsal side of an embryo (differences were considered significant for P<0.01).
Figure 41:
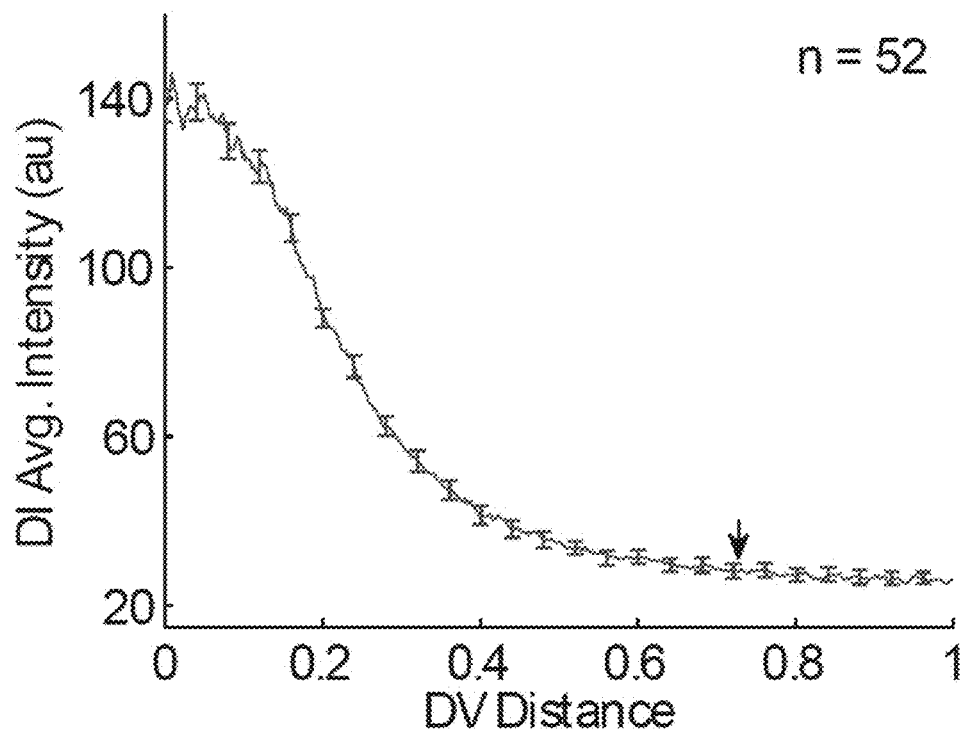
Figure 42:
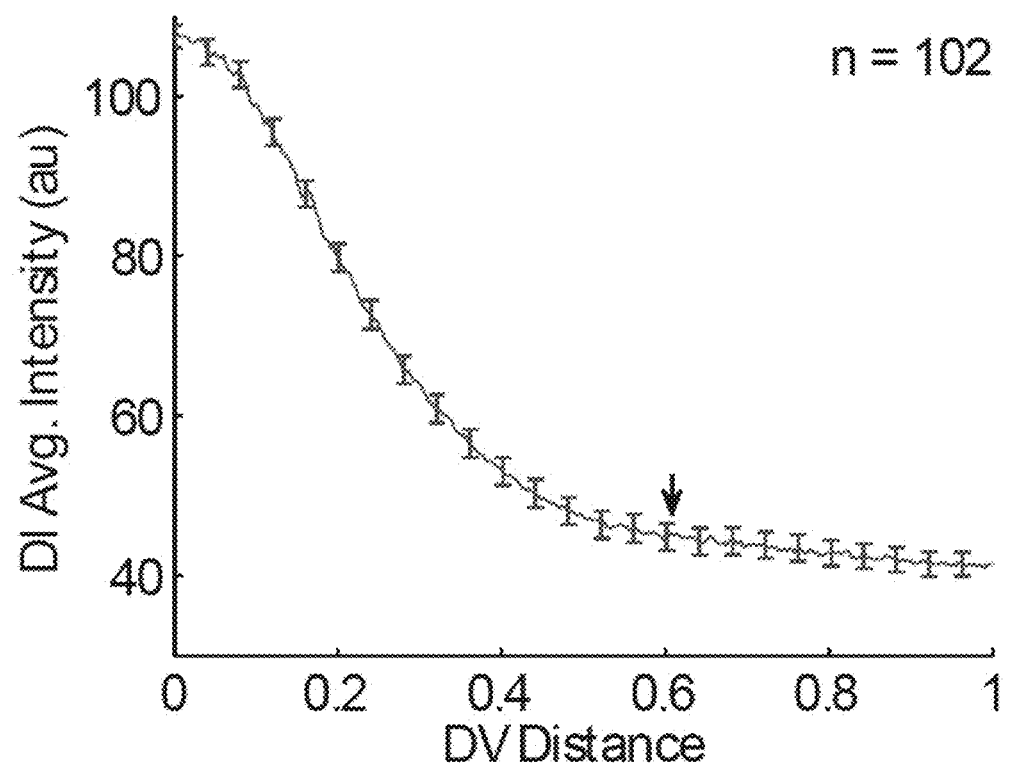
Figure 43:
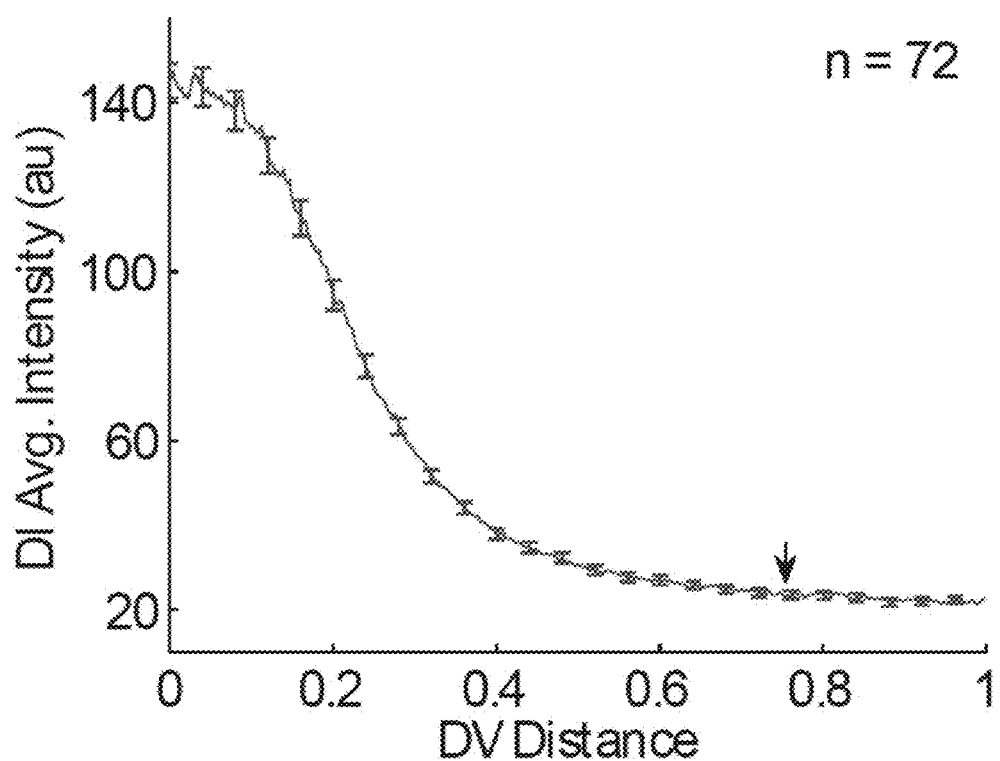

Under flow conditions, embryos at the traps experience non-uniform pressure and shear by the surrounding fluid; the resulting force flips the embryo vertically, inserting it into the cylindrical trap (FIG. 26 and FIGS. 37(a)-(c)). This is achieved entirely passively by hydrodynamics, i.e. without user intervention or control. Once the loading process is completed, the injection pressure is reduced, and the trap opening contracts, securing the embryo inside in an up-right position (with DV axis being parallel to the cover slip, FIG. 26-27). This lock-in feature allows the present device to be disconnected from the rest of the hardware, transported for imaging, or stored with the embryos embedded. Because the operation of the device incorporates two simple steps and does not require computer, valves, or other off-chip components except a pressure source, it can easily be used by non-experts. The present META also does not introduce illumination bias in the embryos (FIG. 38).

META-Based Imaging and Analysis of Pattern Formation

After optimizing and testing the present META device, it analyzed the distribution of the nuclear levels of Dorsal (Dl), a transcription factor that initiates the dorsal-to-ventral (DV) patterning of the Drosophila embryo. The ventral-to-dorsal distribution of nuclear Dl is induced by localized activation of the Toll receptor on the ventral side of the embryo. Prior to Toll activation, Dl is sequestered in the cytoplasm, in a complex with its binding partner Cactus. In response to Toll signaling, Cactus is degraded and Dl moves into the nucleus, where it binds the regulatory regions of its target genes.

One of the outstanding questions in the DV patterning system is the spatial extent of the Dl gradient. More specifically, it is not clear what is the part of the DV axis over which the Dl gradient is flat, and, hence, cannot act as a patterning signal. This has been a matter of intense debate in recent publications. The disagreements in the literature can be traced to the methodological limitations in quantification of the Dl gradient. While end-on imaging provides information about the entire DV axis, it has been limited to only a handful of embryos until this point. The lateral imaging approach, on the other hand, allows for extraction of a larger number of gradients, but it is limited to only a fraction of the DV axis. The present META platform provides a significant increase in the statistical power of end-on imaging and answers the question about the spatial extent of the Dl gradient.

The lowest level of nuclear Dl is at the dorsal-most point, which corresponds to the lowest level of Toll activation. If the level of nuclear Dl at an arbitrary position x along the DV axis is statistically indistinguishable from the nuclear Dl level at the dorsal side of the embryo, then the Dl gradient can be considered flat between the position x and the dorsal-most position. Thus, to estimate the position above which the distribution of nuclear Dl becomes flat, one can compare the distribution of nuclear Dl along the DV axis to the nuclear Dl levels at the dorsal side. Multiple experiments were conducted, collecting dozens of Dl gradients from embryos during the last nuclear division cycle before cellularization in each experiment (FIGS. 38-43). For each of these datasets, a pair-wise statistical test was used to find the DV position at which the mean of the nuclear Dl levels becomes indistinguishable from the value at the dorsal side of the embryo.

Figure 44:
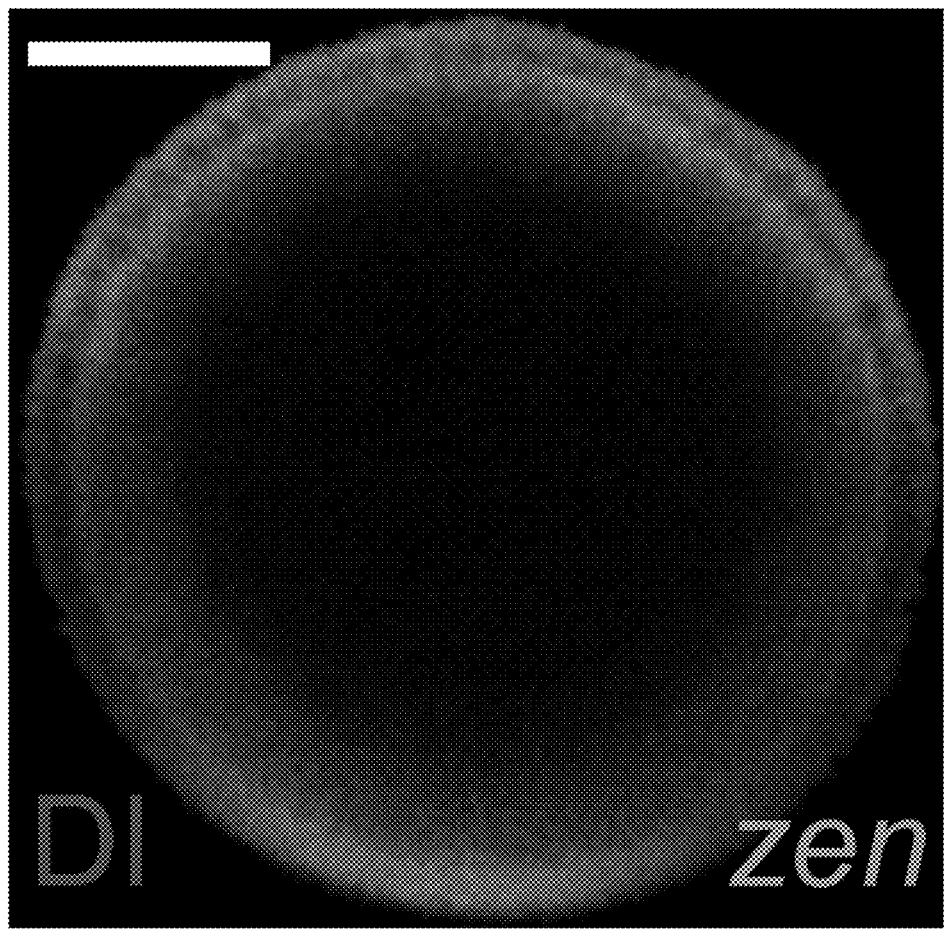
FIG. 44 is (early) and FIG. 45 (late) spatial patterns of Dl and zen expression.
Figure 45:
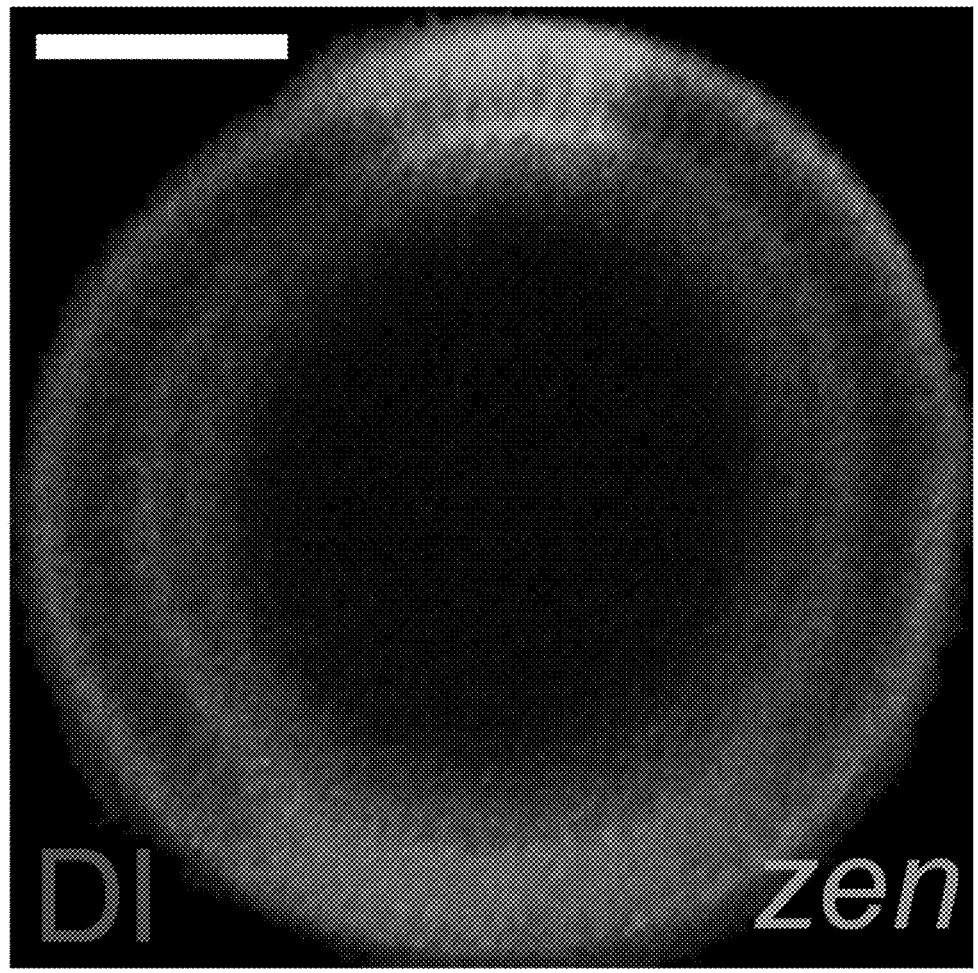
Figure 46:
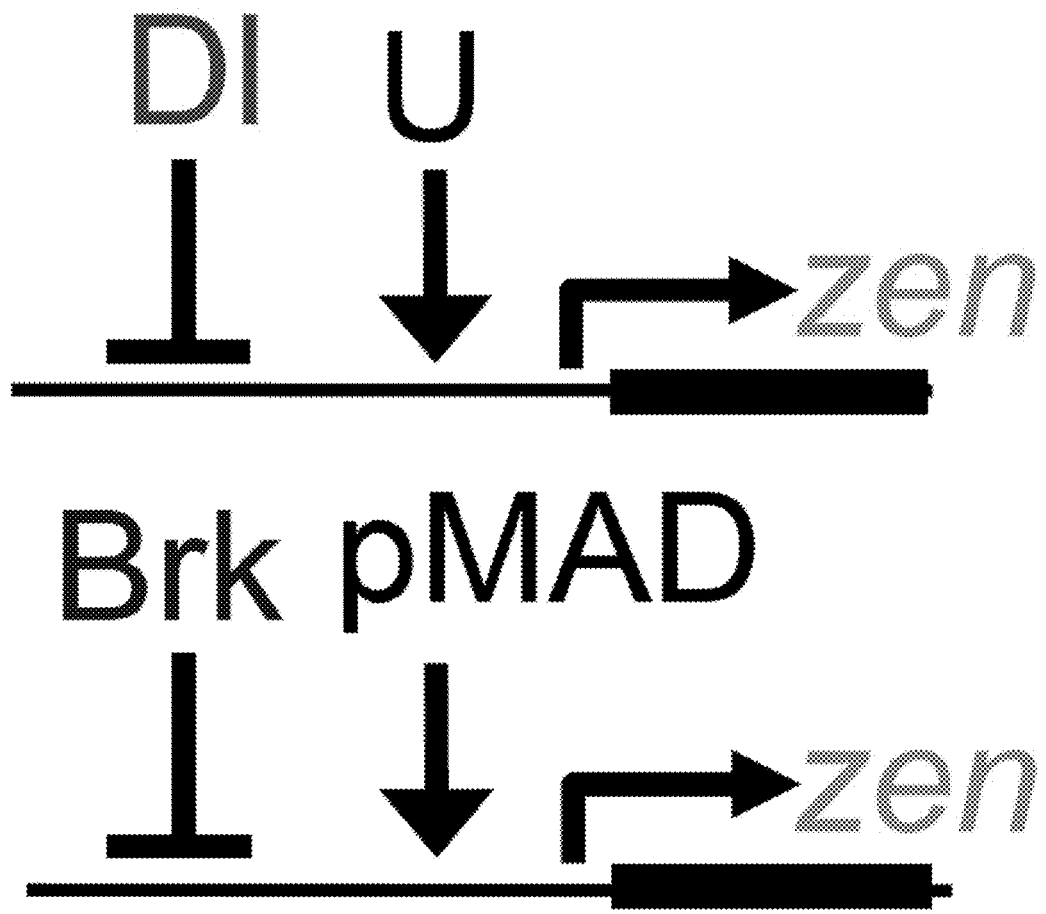
FIG. 46 are schematics of regulatory models that can be used to account for the two phases of zen expression. The schematic for the early expression pattern of zen is shown above, and the late, below.

Based on this analysis, it was found that the nuclear Dl gradient "flatlines" beyond 60% of the DV axis. Thus, any gene expression boundary located outside of this range cannot be explained by a model based on the direct control by the Dl gradient. As an example, consider the regulation of zerknült (zen), a transcription factor expressed on the dorsal side of the embryo. This gene is expressed in a dynamic pattern that first covers the dorsal half of the embryo (FIGS. 44-45). This expression boundary is well within the estimated range of the Dl gradient, which is consistent with the results of previous studies with a transcriptional reporter of zen that contains Dl binding sites. At a later time point, the zen expression boundary moves to ~90% of the DV axis (FIGS. 44-45). The new boundary of the expression domain is outside of the estimated range of the Dl gradient, suggesting a more complex mode of regulation. Indeed, previous studies revealed that the later phase of zen expression depends on Dl only indirectly, through a transcriptional and signaling cascade (FIG. 46).

Figure 47:
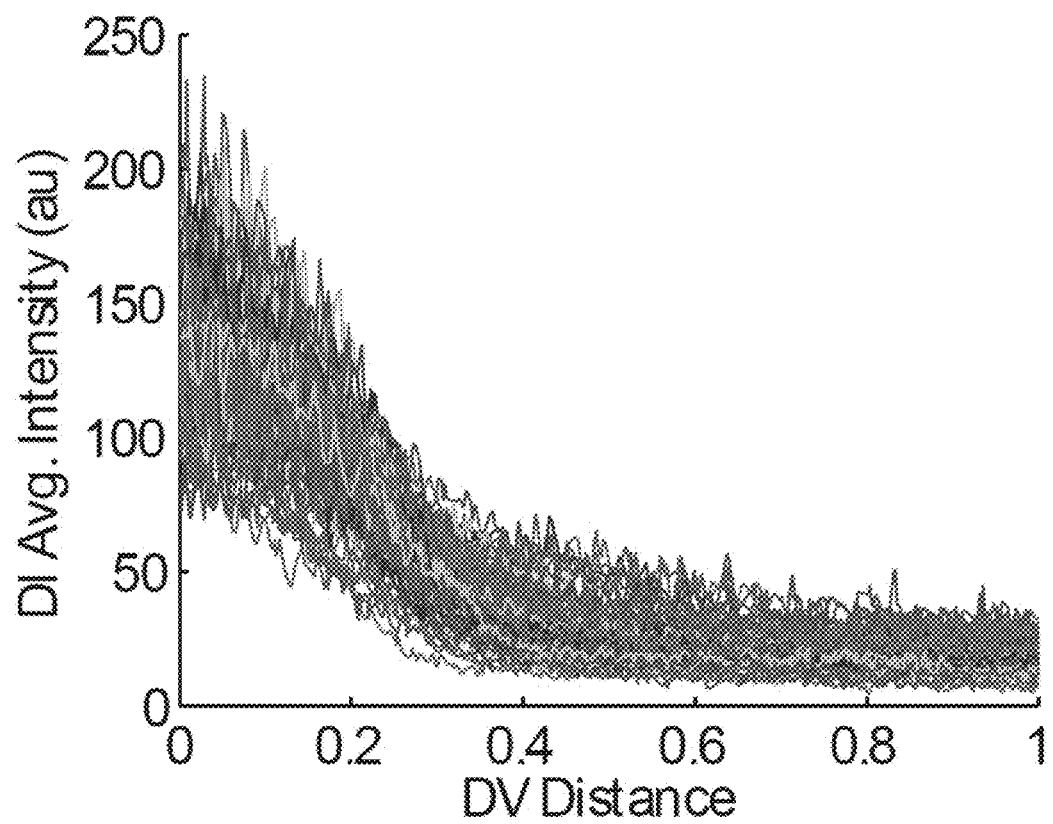
FIGS. 47-49 are pair-wise comparisons of Dl gradients in the wild type and mutant backgrounds. Nuclear Dl gradients from the wild type (FIG. 47) and embryos from dl heterozygous females (FIG. 48) are shown. Embryos were fixed and stained together, loaded onto a microfluidic trap, and imaged in a single imaging session. Wild type embryos carry the histone-GFP insertion and can be easily distinguished from mutant embryos.
Figure 48:
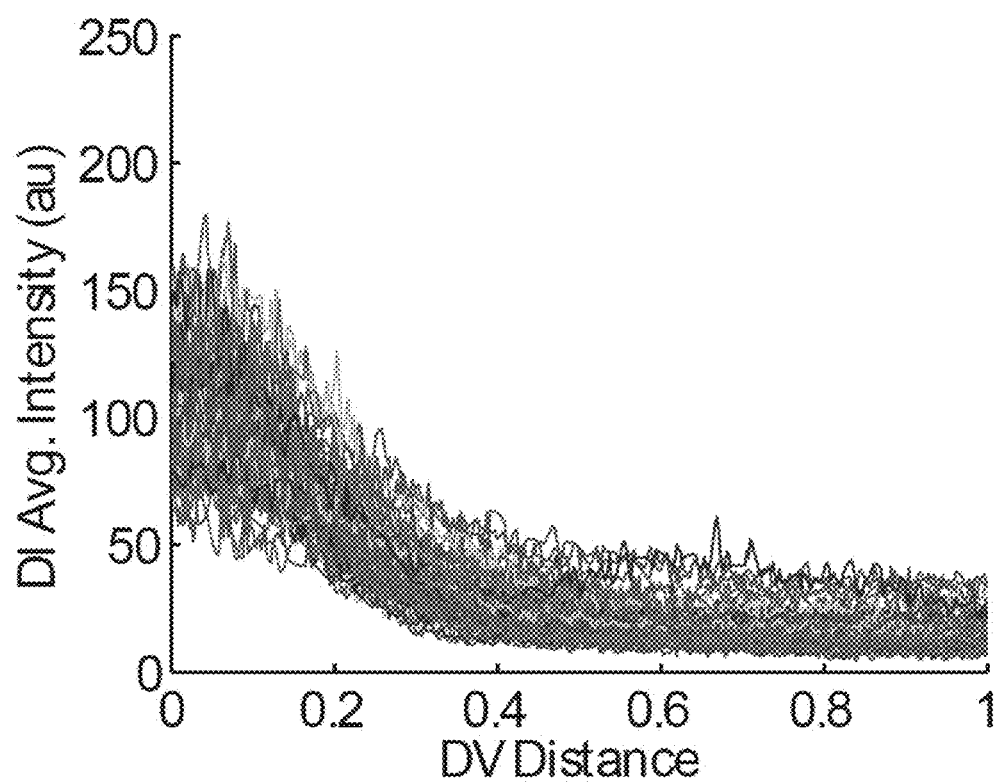
Figure 49:
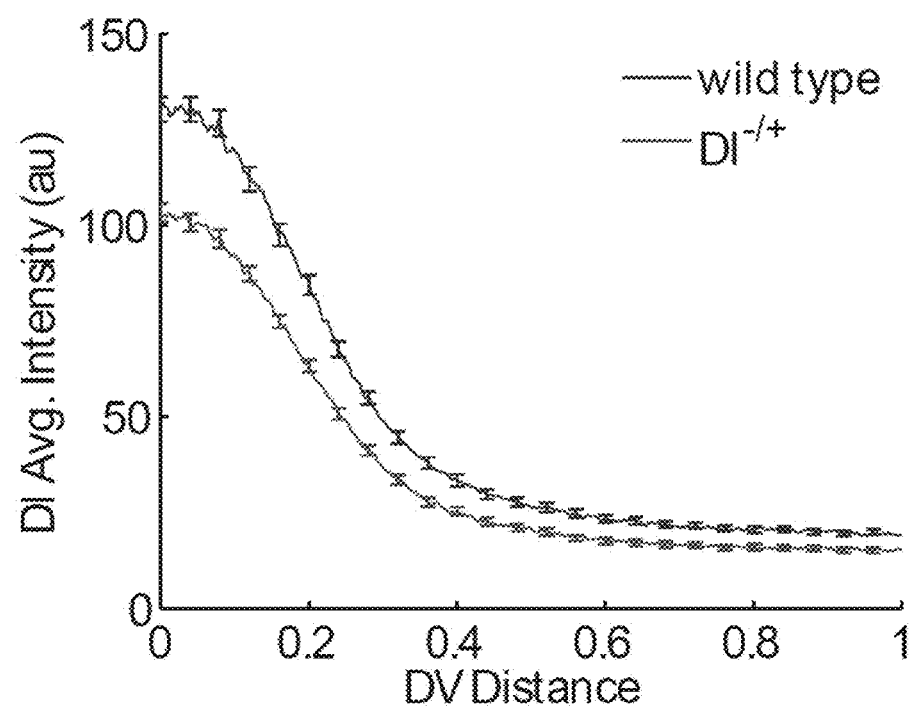

Quantitative analysis of the DV patterning cascade requires systematic analysis of multiple transcriptional and signaling targets of Dl, in both the wild type and mutant backgrounds. META-based imaging can be readily used to statistically compare the spatial pattern of patterning signals across multiple genetic backgrounds. The main idea is based on the simultaneous fixation, staining, and imaging of wild-type embryos and embryos from an arbitrary background. This approach limits or eliminates multiple artifacts associated with numerous steps of the procedure leading to imaging of stained embryos. As an illustration, the Dl gradients extracted from the wild-type embryos and embryos derived from mothers with only a single copy of the dl gene (FIGS. 47-49) show that the nuclear Dl levels in the latter are reduced throughout the DV axis. Note that the nuclear Dl levels are reduced to only 80% of their wild-type value (FIG. 49). In the future, similar experiments can be used to explore the effects of other genetic perturbations of the network that controls nuclear import of Dl.

Figure 50:
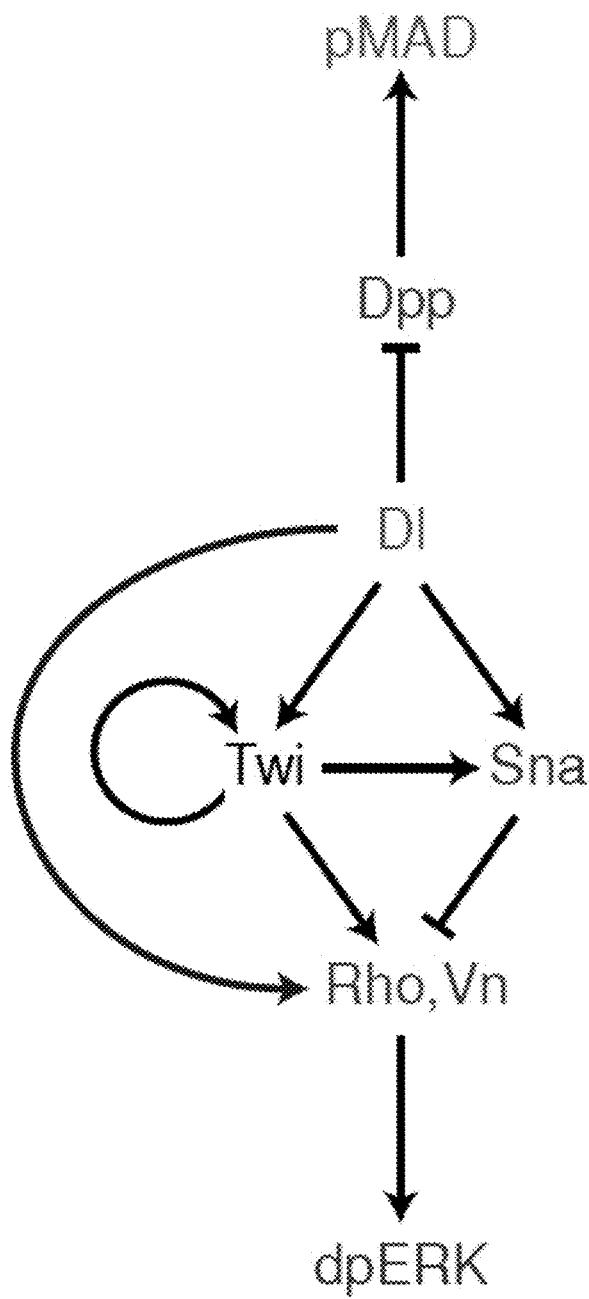
FIGS. 50-56 illustrate signal transduction in DV patterning and morphogen gradients quantitatively characterized using a META according to an exemplary embodiment of the present invention.
Figure 51:
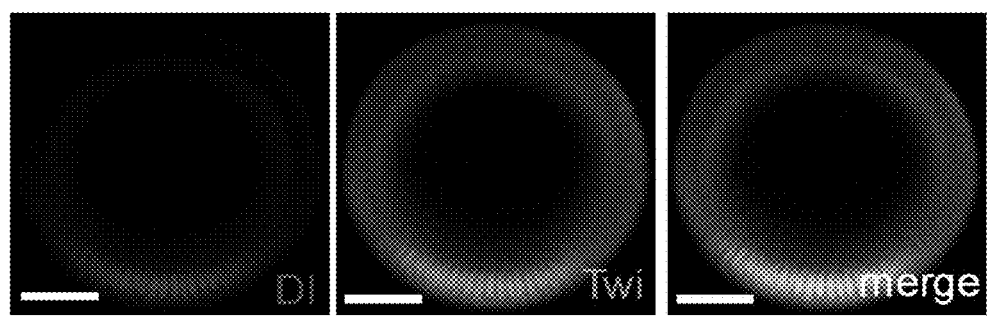
Figure 52:
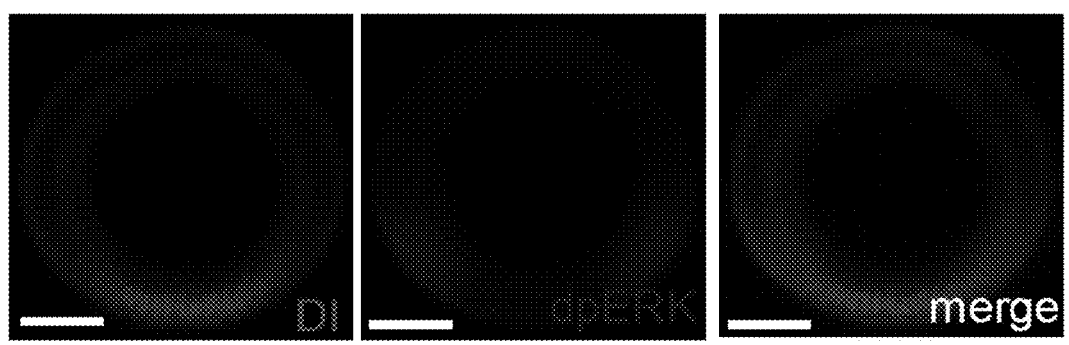
Figure 53:
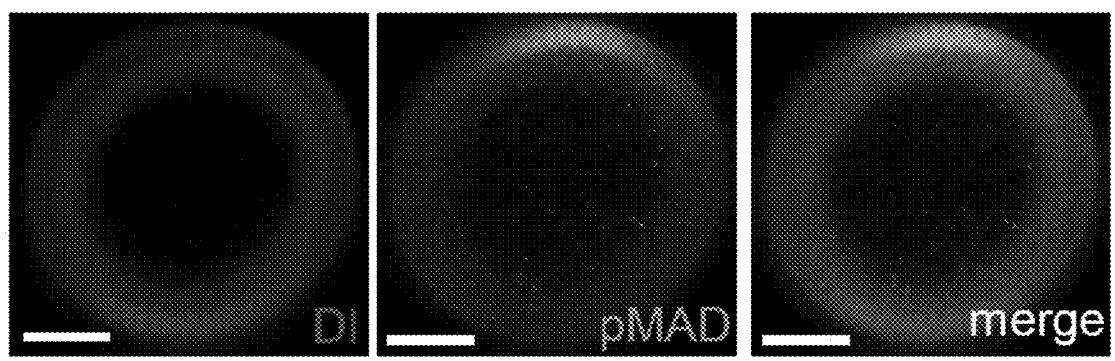
Figure 54:
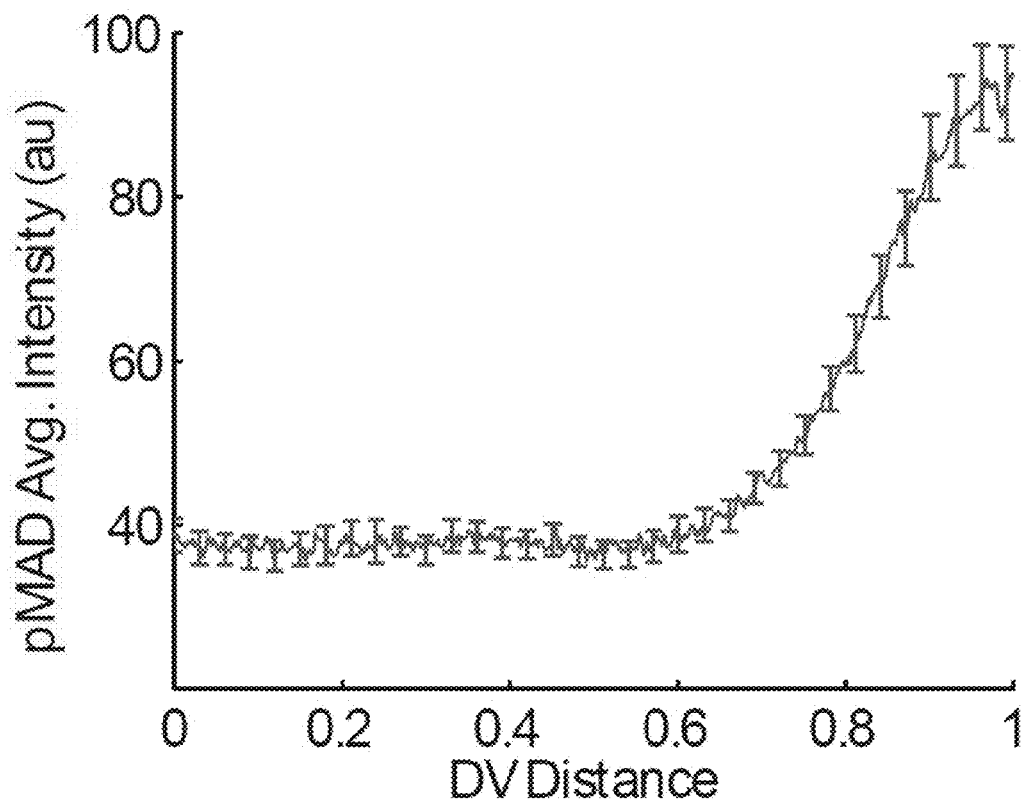
Figure 55:
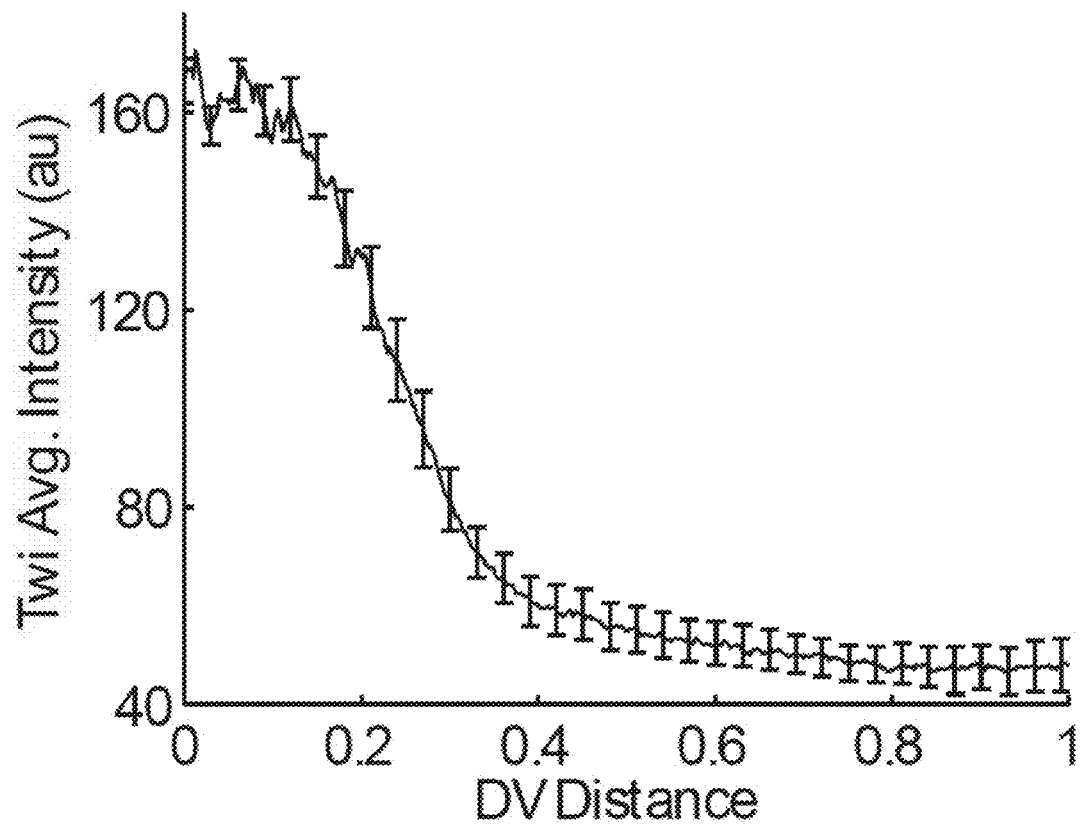

In addition to Dl, the distribution of other regulators of the DV patterning system were analyzed. This system is dominated by feedforward loops, a network motif in which a gene is controlled both by the primary input, such as Dl, and by one of its more proximal targets (FIG. 50). For instance, Snail (Sna), a transcription factor expressed in the future mesoderm, is activated both by Dl and by Twist (Twi), a transcription factor that is directly activated by Dl. Patterning of the neurogenic ectoderm requires a two-peaked pattern of signaling through the Mitogen Activated Protein Kinase (MAPK) cascade. This pattern reflects the localized expression of the Epidermal Growth Factor Receptor pathway components, which are activated by Dl and Twi and repressed by Sna. Finally, the dorsal ectoderm is patterned by the gradient of signaling through the Bone Morphogenetic Protein (BMP) pathway, spatially regulated by Dl and its multiple targets.

Figure 56:
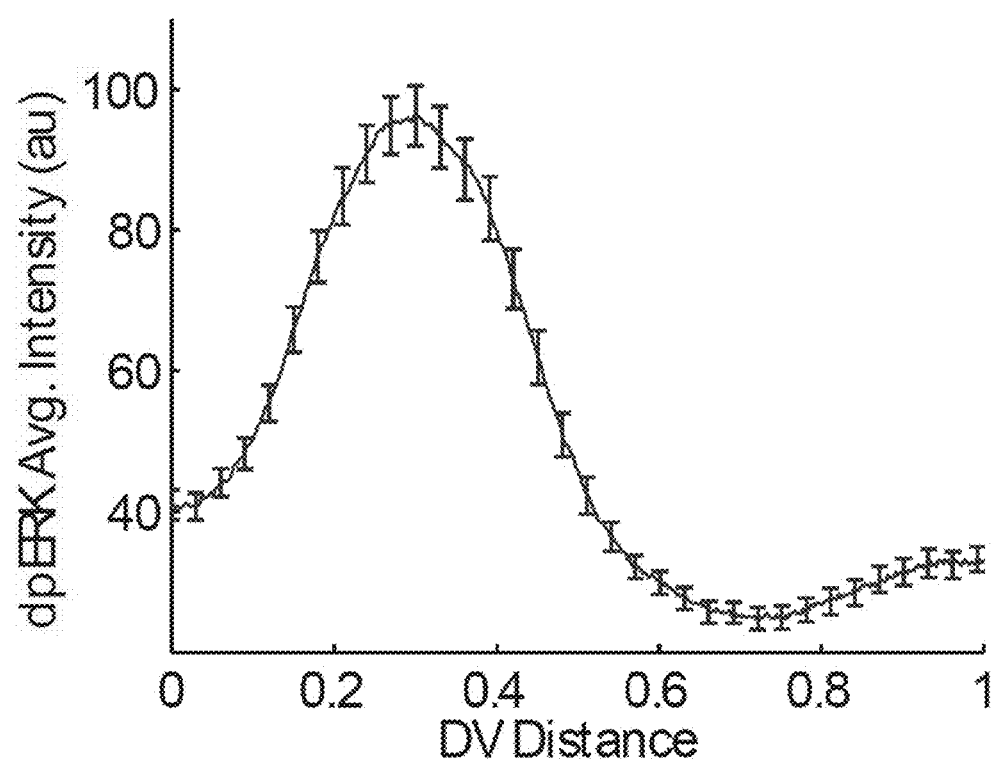

The gradient of Twi, as well as the gradients of the MAPK and BMP signaling, was characterized using the present META (FIGS. 51-56). Twi and BMP signaling gradients are consistent with the ones reported elsewhere, but the MAPK phosphorylation gradient (dpERK) is quantified here for the first time, revealing a significant level of MAPK activation at the ventral-most region of the embryo (FIG. 56). To test whether the ventral levels of MAPK activation are significant, the pattern of Cic, a transcriptional repressor that is degraded as a consequence of its phosphorylation by MAPK, was examined. We found Cic is significantly down-regulated at the ventral side of the embryo (data not shown), supporting the notion that the ventrally activated MAPK contributes to the DV patterning. Thus, META-based imaging provides quantitative characterization of the Dl gradient and identifies new features of the DV patterning system.

Discussion

The present microfluidic platform for high-throughput end-on imaging of *Drosophila* embryos has been successfully tested. This approach dramatically increases the efficiency of collecting and analyzing the signaling and transcriptional patterns along the DV embryonic axis. Until now, end-on imaging required manipulation of individual embryos and, hence, was not ideally suited for the quantitative and statistical studies of pattern formation. Using the present microfluidic embryo trapping array, hundreds of embryos can be oriented in an upright position in a matter of minutes. Datasets from dozens of embryos are sufficient for statistical analysis of spatial patterns in both the wild type and mutant backgrounds. Thus, large-scale analysis of positional information in the DV system is now possible.

Figure 57:
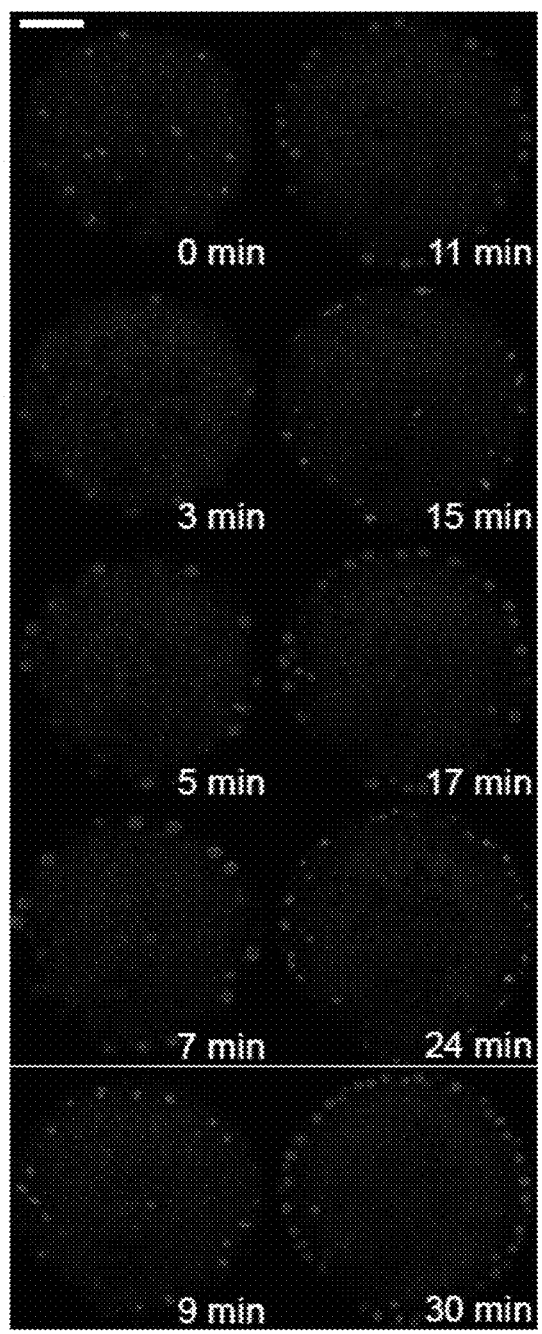
FIGS. 57-58 show live imaging of embryos in a META according to an exemplary embodiment of the present invention. Live embryos expressing nuclear histone-GFP can be imaged for extended periods.
Figure 58:
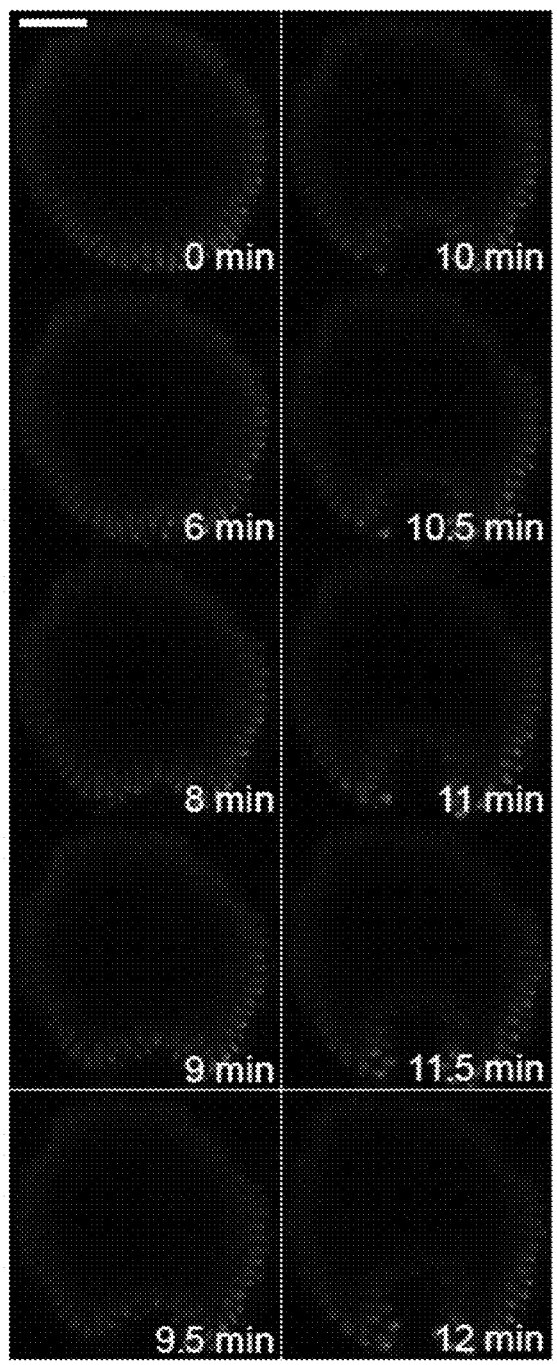

In the future, the temporal resolution of end-on imaging can be increased by grouping the images collected from fixed samples into distinct temporal classes. This can be based on cytological markers, such as the nuclear density in the syncytium or the extent of membrane invagination during cellularization. Furthermore, in preliminary experiments it was established that live embryos can be successfully loaded into and imaged in the present META device. As a demonstration, videos of cell divisions in the early embryo as well as an embryo undergoing gastrulation were obtained (FIGS. 57-58). Thus, the present META platform can be used to work with both fixed and live samples.

Unlike the anterorposteior (AP) patterning system, which has been a subject of extensive mathematical modeling and computational analysis, comprehensive quantitative models of the DV system are yet to be developed. This is now a feasible goal, enabled by the efficiency of end-on imaging enabled by the present META platform. Given the collection of spatiotemporal patterns of multiple network components in multiple genetic backgrounds, it should be possible to formulate increasingly mechanistic models of the DV patterning system as modeling of the DV system presents a number of new challenges, such as the need to integrate the transcriptional and extracellular layers of regulation.

META-based imaging is not limited to the analysis of pattern formation in the early embryo. Other related developmental events, such as gastrulation, can be readily analyzed using this system. In addition, META for related fly species can be readily designed by modifying the trap size for embryos that are smaller or larger than those of *D. melanogaster*. Finally, because it has been shown that a general method for handling non-spherical objects (which is significantly more difficult than handling cells) is possible, similar microfluidic designs can be used to image pattern formation and morphogenesis in other model organisms of developmental genetics.

On-Line Methods

Microfluidic Device Fabrication

A mold was first fabricated by photolithographic processes. In a first step, a negative photoresist (SU8-2100, Microchem) was spin-coated twice at 400-600 rpm onto a silicon wafer to form a ~500 µm-thick layer. Features on a transparency mask were transferred to the SU-8 coated wafer by standard UV photolithography. The mold was then treated with tridecafluoro-1,1,2,2-tetrahydrooctyl-1-trichlorosilane vapor (United Chemical Technologies) in a vacuum desiccator to prevent adhesion of PDMS during the molding process.

For fabricating the PDMS devices, a mixture of PDMS (parts A and B in 15:1 ratio) was poured onto the mold to give a ~1 mm-thick layer and partially cured at 70° C. for 20 min. A mixture of PDMS (part A and B in 10:1 ratio) was then poured on top to form ~4 mm-thick layer and cured at 70° C. for two hours. After peeling off the 5 mm PDMS layer, the individual devices were cut out, and access holes were punched in the PDMS. The devices were then treated with oxygen plasma and bonded to a cover glass.

Microfluidic Device Operation

*Drosophila* embryos suspended in 100 mL PBS buffer in a glass bottle were connected to the inlet of the present META. The outlet of the device was connected to a long PE90 tubing. The high resistance of the long PE90 tubing makes the pressure drop along the device less than 20% of the total pressure drop. This allows the traps expand uniformly throughout the device. To load the embryo suspension into the device, a constant pressure source (~6 psig) was applied to drive the flow into the device. Precise pressure is not critical. After loading, the injection pressure was slowly decreased to 0 psig. All tubings were then disconnected from the device for imaging and storage.

Confocal microscopy was performed on a Zeiss LSM 510 VIS Confocal Microscope. The device was filled with fluorescent dextran (70,000 MW, Oregon Green, Invitrogen) solution. The pressure (0 psig to 6 psig) was controlled using a portable air compressor. Note that during normal operation of the device, however, a thumb-driven syringe to approximate this pressure range or a tank of compressed gas would also serve the same purpose.

Fly Strain and Whole-Mount Immunostaining

OreR flies were used as a wild type strain and dl[6] flies were used as dl heterozygous mutant strain in this study. Flies were raised and embryos were collected at 25° C. Antibody staining was performed as described previously. The following primary antibodies were used: rabbit anti-dpERK (1:100, Cell Signaling), mouse anti-Dorsal (1:100, Developmental Hybridoma Bank), guinea pig anti-Twist (1:40, a gift from M. Levine), and rabbit anti-phospho-SMAD (1:3500, a gift from D. Vasiliauskas, S. Morton, T. Jessell and E. Laufer, Columbian University). DAPI (1:10,000) was used to stain nuclei and Alexa Fluors (1:500, Invitrogen) were used as secondary antibodies.

To visualize zen transcript, fluorescence in-situ hybridization was used. Embryos were hybridized with DIG-labeled antisense probe to zen mRNA for overnight at 60° C. Sheep anti-DIG (1:20, Roche) was used as primary antibody and Alexa Fluors (1:500, Invitrogen) were used as secondary antibodies.

Microscopy and Gradient Quantification

Imaging was performed on a Zeiss LSM510 confocal microscope with a Zeiss 20× (NA 0.6) A-plan objective. High-resolution images (1024×1024 pixels, 12 bits depth) were obtained from the focal plane ~70 μm from anterior or posterior pole. For live-imaging, LEICA SP5 confocal microscope was used with 63× (NA 1.3) glycerin objective. Images were obtained every seven seconds from the focal plane ~70 μm from the anterior pole.

Protein gradients were extracted from confocal images by using a Matlab program. DAPI staining was used to determine the positions of nuclei, which were then used to quantify the nuclear gradient of the protein of interest. The embryos were also co-stained with Dl in order to determine the ventral most point of the embryo. Briefly, the extracted nuclear Dl gradient was fitted with a Gaussian curve and the raw data were oriented such that the maximum of the Gaussian fit was set as the ventral most point of the embryo, i.e. x=0.

Characterization of Flow Profile in the Micro Device by Numerical Simulation

Figure 29:
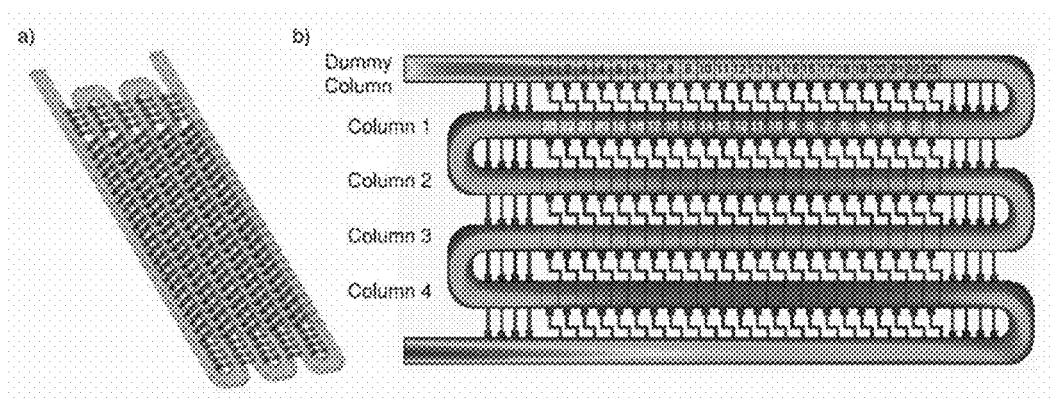
FIGS. 29(a) and (b) show flow profile from numerical simulations according to exemplary embodiments of the present invention, where.
FIG. 29(b) shows flow profile at the vertical middle plane of the device of FIG. 29(a) (280 μm from the bottom of the channel).

Simulations were performed using a commercial finite element package, COMSOL®. A three-dimensional geometry of a section of the device used is shown in FIG. 29a. The actual geometry was simplified to reduce the number of mesh elements. Incompressible steady-state Navier-Stokes equations were solved. The pressure at the outlet was fixed at atmospheric pressure, and the pressure at the inlet was set to obtain a volumetric flow rate equal to the measured value.

Characterization of Hydrodynamic Force on an Embryo by Numerical Simulation

The simulation was used to calculate hydrodynamic force on an embryo located in a trap. The embryo was simplified as described in FIG. 30 at 60° C. to the trap inlet. The total force in the x-direction was calculated using the post processing feature of COMSOL®, which results in a torque.

The specific configurations, choice of materials, and the size and shape of various elements can be varied according to particular design specifications or constraints requiring a device, system, or method constructed according to the principles of the invention. Such changes are intended to be embraced within the scope of the invention. The presently disclosed embodiments, therefore, are considered in all respects to be illustrative and not restrictive. The scope of the invention is indicated by the appended claims, rather than the foregoing description, and all changes that come within the meaning and range of equivalents thereof are intended to be embraced therein.

What is claimed is:

1. A microfluidic cell trap array comprising:
   a cell-delivery channel defined between channel walls, the channel having an inlet and an outlet; and
   cell traps formed in at least a portion of the channel walls such that each cell traps comprise a cavity to trap a cell therein;
   wherein the cell trap array has a density of greater than 800 traps/mm$^2$.

2. The microfluidic cell trap array of claim 1, wherein the cell trap array has a loading efficiency of greater than 70%.

3. The microfluidic cell trap array of claim 1, wherein cell trap array has a loading efficiency of greater than 90%.

4. The microfluidic cell trap array of claim 1, wherein the cell-delivery channel comprises a generally serpentine channel.

5. The microfluidic cell trap array of claim 4, wherein the generally serpentine channel comprises a plurality of generally parallel subchannels connected to one another via subchannel end portions.

6. The microfluidic cell trap array of claim 5, wherein the subchannel end portions have an appropriate curvature such that the generally serpentine channel with a plurality of generally parallel subchannels provides for a generally uniform medium flow rate therethrough.

7. The microfluidic cell trap array of claim 1, wherein:
   the cell-delivery channel forms a serpentine channel including a plurality of switchback subchannels connected to one another via subchannel end portions;
   wherein at least a portion of the total number of subchannels have a cell trapping zone along the length of a subchannel, the cell trapping zone bounded by a leading cell focusing zone and a trailing cell focusing zone;
   wherein in each cell trapping zone, the cell traps comprise a plurality of single-cell traps sized to capture a single cell; and
   wherein each cell focusing zone comprises a plurality of flowthrough apertures sized so as not to capture a cell flowing therethrough, such that media having cells traveling through a subchannel having a cell trapping zone will experience both a flow parallel to the length of the subchannel to carry cells through the array, and a normal flow moving travelling cells closer to the traps in the cell trapping zone after passing the leading cell focusing zone.

8. The microfluidic single-cell trap array of claim 7, wherein at least a portion of the single-cell traps have a geometry engineered so that traps experience similar flow rates near one another in order to provide a generally uniform trapping condition for each trap.

9. The microfluidic single-cell trap array of claim 7, wherein at least a portion of the single-cell traps have a geometry engineered so that once a cell occupies a trap, it physically excludes another cell from being trapped in the same trap.

10. The microfluidic single-cell trap array of claim 7, wherein at least a portion of the single-cell traps have a geometry engineered so that once a cell occupies a trap, neither the media flow through the single-cell trap array nor another cell can dislodge a trapped cell.

11. The microfluidic single-cell trap array of claim 7, wherein after passing a cell focusing zone, travelling cells in proximity to a single-cell trap experience two flows, a main stream (Q) flowing in the direction of the cell-delivery channel, and a directing stream (q) directing the cell into a single-cell trap; and
   wherein the ratio Q/q is engineered to guide cells into non-occupied traps, and once all traps in a subchannel having a cell trapping zone contain trapped cells, travelling cells pass a downstream cell focusing zone, and travel to a next subchannel.

12. The microfluidic cell trap array of claim 1, wherein at least a portion of the cell traps comprise a non-reactive surface that form a cavity to capture a cell within the cavity without biochemical interaction between a cell and the non-reactive surface.

13. The microfluidic cell trap array of claim 1, wherein at least a portion of the cell traps comprise traps formed by walls separated by a gap so each such trap forms a cavity that is sized to provide a surface area that can only trap a single cell.

14. The microfluidic cell trap array of claim 1, wherein at least a portion of the cell traps comprise traps formed by walls separated by a gap so each such trap forms a cavity that is shaped to provide a surface area that can only trap a single cell.

15. A microfluidic cell trap array comprising:
   a cell-delivery channel having an inlet and an outlet, the cell-delivery channel forming a serpentine channel including a plurality of switchback subchannels connected to one another via subchannel end portions; and
   cell traps formed in a wall of the channel;
   wherein the cell traps formed in a wall of the channel comprise a plurality of single-cell traps formed in at least a portion of the total number of subchannels, such that single-cell traps each comprise a cavity to trap a cell therein;
   wherein the cell trap array comprises a single-cell trap array having the density of greater than 800 traps/mm$^2$; and
   wherein the single-cell trap array has a loading efficiency of greater than 70%.

16. The microfluidic cell trap array of claim 15, wherein in at least a portion of the total number of subchannels having single-cell traps, such subchannels have a cell trapping zone along the length of the subchannel, and a cell focusing zone on at least one side of the cell trapping zone.

17. The microfluidic cell trap array of claim 16, wherein the subchannels having a cell trapping zone have a cell focusing zone on both sides of the cell trapping zone.

18. The microfluidic cell trap array of claim 16, the cell trapping zone comprising at least a portion of the single-cell traps, the single-cell traps sized to capture a single cell, and the cell focusing zone comprising flowthrough apertures sized so as not to capture a cell flowing therethrough.

* * * * *